(12) United States Patent
Pirrung et al.

(10) Patent No.: US 7,057,052 B2
(45) Date of Patent: Jun. 6, 2006

(54) HETEROCYCLIC QUINONES AS PHARMACEUTICAL AGENTS

(75) Inventors: Michael C. Pirrung, Chapel Hill, NC (US); Johannes Rudolph, Durham, NC (US)

(73) Assignee: Duke University, Durham, NC (US)

( * ) Notice: Subject to any disclaimer, the term of this patent is extended or adjusted under 35 U.S.C. 154(b) by 124 days.

(21) Appl. No.: 10/255,897

(22) Filed: Sep. 26, 2002

(65) Prior Publication Data

US 2004/0063774 A1    Apr. 1, 2004

(51) Int. Cl.
*C07D 209/12* (2006.01)
*C07D 209/34* (2006.01)

(52) U.S. Cl. .................. 548/452; 548/469; 548/486; 548/509

(58) Field of Classification Search .............. 548/452, 548/509, 469, 486
See application file for complete search history.

(56) References Cited

U.S. PATENT DOCUMENTS

| | | | |
|---|---|---|---|
| 5,780,496 A | 7/1998 | Tang et al. | |
| 5,786,488 A | 7/1998 | Tang et al. | |
| 6,011,058 A | 1/2000 | Zalkow et al. | |

FOREIGN PATENT DOCUMENTS

| | | |
|---|---|---|
| WO | WO 96/40115 | 12/1996 |
| WO | WO 01/09373 | 2/2001 |
| WO | WO 01/16300 | 3/2001 |
| WO | WO 01/21589 | 3/2001 |
| WO | WO 01/27077 | 4/2001 |

OTHER PUBLICATIONS

Pirrung et al., Organic Letters, vol. 3, No. 3, pp. 365-367, (2001).*
Lion et al., J. Heterocyclic Chem., vol. 39, pp. 125-130, Jan.-Feb. (2002).*
Bardyshev et al., Girdoliznaya i Lesokhimicheskaya Promyshlennost, vol. 20, No. 8, apges 10-12, (1967), abstract only.*
Harris, G. Davis Jr., et al., *A One-Pot, Two-Step Synthesis of Tetrahydro Asterriquinone E, Organic Letters*, vol. 1, No. 3, pp. 431-433 (1999).
Alvi, Khisal A., et al., *Asterriquinones Produced by Aspergillus candidus Inhibit Binding of the Grb-2 Adapter to Phosphorylated EGF Receptor Tyrosine Kinase, The Journal of Antibiotics*, vol. 52, No. 3, pp. 215-223 (Mar. 1999).
Ono, Katsuhiko, et al., *Inhibition of HIV-Reverse Transcriptase Actibity by Asterriquinone and Its Analogues, Biochemical and Biophysical Research Communications*, vol. 174, No. 1, pp. 56-62 (Jan. 15, 1991).

* cited by examiner

*Primary Examiner*—Kamal A. Saeed
*Assistant Examiner*—Rebecca Anderson
(74) *Attorney, Agent, or Firm*—Myers Bigel Sibley & Sajovec

(57) ABSTRACT

Pyrrolylquinones and indolylquinones useful for treating diseases such as neurodegenerative disease, viral infections and proliferative disease are described, along with methods of making such compounds and pharmaceutical formulations containing such compounds.

9 Claims, No Drawings

HETEROCYCLIC QUINONES AS PHARMACEUTICAL AGENTS

FIELD OF THE INVENTION

This invention relates to synthetic methods for the preparation of pyrrolylquinones and indolylquinones, the compounds so prepared, and uses thereof in the treatment of disease.

BACKGROUND OF THE INVENTION

Demethylasterriquinone is a natural product that was discovered by Merck to have the ability to activate the insulin receptor, and thereby to act orally in glucose lowering in mouse models of diabetes. They have also shown that this compound can activate the TrkA nerve growth factor (neutrophin) receptor. They have further developed a synthetic version identified as "Compound 2" below. See generally Zhang et al., Science 284, 974–977 (1999); Liu et al., J. Med. Chem. 43, 3487–3494 (2000).

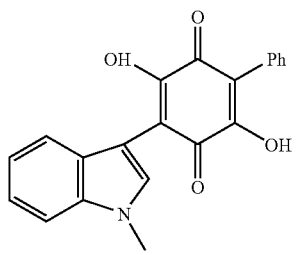

Compound 2

U.S. Pat. No. 5,786,488 to Tang et al. proposes synthesis of mono- and bis-indolylquinones using alkali conditions and metal carbonates.

Harris, et al., *A One-Pot, Two-Step Synthesis of Tetrahydro Asterriquinone E*, Organic Letters 1999, 1(3):431–433 discusses a procedure similar to the '488 patent to produce asterriquinone E.

U.S. Pat. No. 5,780,496 to Tang et al. proposes the utility of indolylquinones as agents for treatment of protein tyrosine kinase cell proliferative disorders.

U.S. Pat. No. 6,011,058 to Zalkow et al. proposes targeting Cdc25 with seco-cholestane derivatives.

Ono et al., *Inhibition of HIV-Reverse Transcriptase Activity by Asterriquinone and its Analogues*, Biochem. Biophys. Res. Commun. 1991, 174(1):56–62, discusses the ability of asterriquinone and asterriquinone derivatives B1-4, C1-1 and D-1 to inhibit HIV-reverse transcriptase.

U.S. Pat. No. 6,376,529 to Tang et al. proposes the use of monoindolylquinones and bisindolylquinones to treat PTK-related cell proliferative disorders and diabetes mellitus.

SUMMARY OF THE INVENTION

A first aspect of the present invention is an acid-catalyzed method of producing a compound of Formula I:

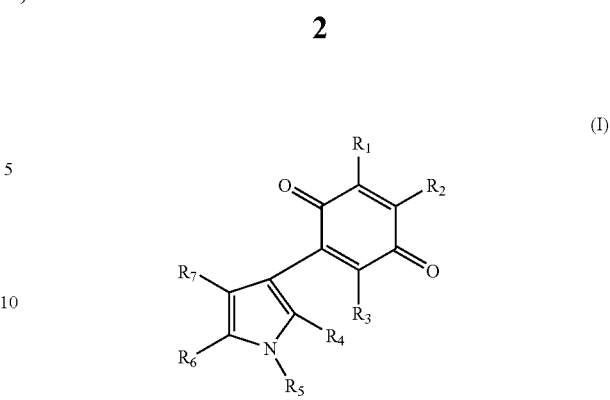

wherein:

$R_1$ and $R_3$ are each independently hydrogen, OH, SH, halo, amino, alkoxy, aminoalkyl, alkyl, aryl, acyloxy, or (acyloxy)alkyl $R_2$ is hydrogen, aryl, heteroaryl, indolyl, alkyl, alkoxy, phenoxy, anilino, amino, halo, acyloxy, or (acyloxy)alkyl;

or $R_1$ and $R_2$ together form an aromatic ring (e.g., R1 and R2 together form —CH=CH—CH—, —CH=CH—CH=CH—, or —CH=CH—CH=CH—CH=CH—);

$R_5$ is hydrogen, $C_1$–$C_7$ alkyl, $C_2$–$C_7$ alkenyl, $C_2$–$C_7$ alkynyl, arylalkyl, or aryl;

$R_4$ is hydrogen, branched or unbranched saturated $C_1$–$C_n$ alkyl, branched or unbranched unsaturated $C_1$–$C_n$ alkyl, alkylcarboxy, $C_2$–$C_m$ alkenyl, alkynyl, alkenylcarboxy, aryl, alkylaryl hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 2–12, preferably 2–7, and m is an integer from 3–12, preferably 3–7; and $R_6$ and $R_7$ are each independently hydrogen, cycloalkyl, alkyl, alkoxy, halo, aryl, heteroaryl, phenoxy, anilino, amino, or form part of an aromatic ring ((e.g., R6 and R7 together form —CH=CH—CH—, —CH=CH—CH=CH—, or —CH=CH—CH=CH—CH=CH—) wherein said aromatic ring may be unsubstituted or substituted 1, 2 or 3 times with cycloalkyl, alkyl, alkoxy, halo, aryl, heteroaryl, phenoxy, anilino, amino;

which method comprises:

reacting a substituted or unsubstituted 2,5-dichloro-1,4-benzoquinone compound of the formula:

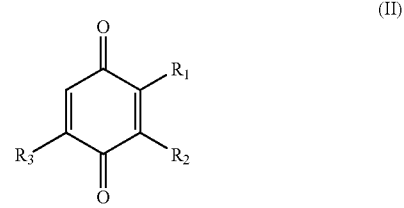

wherein $R_1$, $R_2$ and $R_3$ are as defined above;

with at least one pyrrole of the formula:

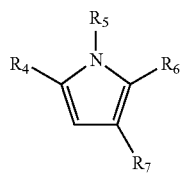

(III)

wherein $R_4$–$R_7$ are as defined above, in a polar organic solvent and in the presence of an acid to produce a first intermediate; and then reacting the first intermediate with an oxidization agent to produce said compound of formula I. In some embodiments of the foregoing, n is 2–7 and m is 3–7. In some embodiments, the method further comprises: reacting said compound of formula I with an alkali metal hydroxide to produce a compound of the formula:

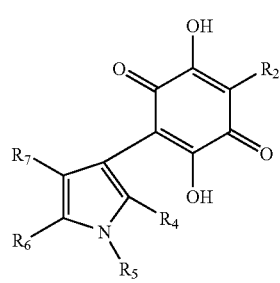

(IV)

wherein $R_2$ and $R_4$–$R_7$ are as defined above. The organic solvent may be, for example, an aprotic solvent selected from the group consisting of tetrahydrofuran (THF), acetonitrile, and mixtures thereof. In some embodiments, the acid may be HCl, $H_2SO_4$, AcOH (acetic acid), or mixtures thereof. In some embodiments the oxidization agent is dichlorodicyanobenzoquinone, $Ag_2CO_3$, or mixtures thereof. The reaction may be conducted at any suitable temperature, such as from about –10° C. to about 100° C.

A second aspect of the present invention is an acid-catalyzed method of producing a compound of formula V:

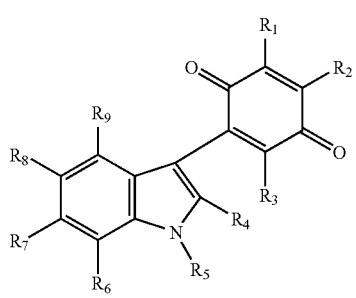

(V)

wherein:

$R_1$ and $R_3$ are each independently OH, SH, halo, amino, alkoxy, aminoalkyl, hydrogen, alkyl, aryl, acyloxy, or (acyloxy)alkyl;

$R_2$ is hydrogen, aryl, heteroaryl, indolyl, alkyl, alkoxy, phenoxy, anilino, amino, halo, acyloxy, or (acyloxy)alkyl; or $R_1$ and $R_2$ can constitute part of an aromatic ring (e.g., R1 and R2 together form —CH=CH—CH—, —CH=CH—CH=CH—, or —CH=CH—CH=CH—CH=CH—);

$R_5$ is hydrogen, $C_1$–$C_7$ alkyl, $C_2$–$C_7$ alkenyl, $C_2$–$C_7$ alkynyl, arylalkyl, or aryl; and $R_4$ and $R_6$–$R_9$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 2–12, and m is an integer from 3–12;

which method comprises:

reacting a substituted or unsubstituted 2,5-dichloro-1,4-benzoquinone compound of the formula:

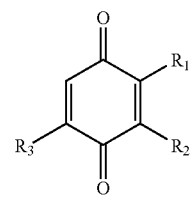

(II)

wherein $R_1$, $R_2$ and $R_3$ are as defined above;

with at least one indole of the formula:

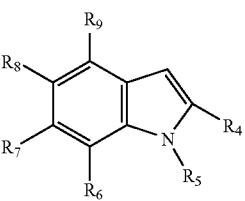

(VI)

wherein $R_4$–$R_9$ are as defined above;

in a polar organic solvent and in the presence of an acid to produce a first intermediate; and then reacting the first intermediate with an oxidization agent to produce said compound of formula V. In some embodiments, n is 2–7 and m is 3–7. The method may further comprise reacting said compound of formula I with an alkali metal hydroxide to produce a compound of the formula:

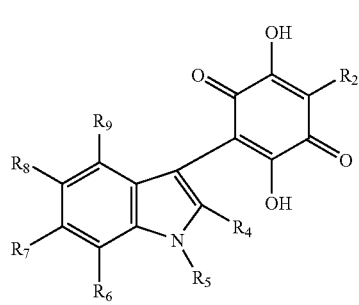

(VII)

wherein $R_2$ and $R_4$–$R_9$ are as defined above. In some embodiments, the organic solvent is an aprotic solvent selected from the group consisting of tetrahydrofuran (THF), acetonitrile, and mixtures thereof. The acid may, for example, be HCl, $H_2SO_4$, AcOH, or mixtures thereof. The oxidization agent may be dichlorodicyanobenzoquinone, $Ag_2CO_3$ or combinations thereof. The reaction may in some embodiments be conducted at a temperature from about −10° C. to about 100° C.

A further aspect of the present invention is a compound of the formula I:

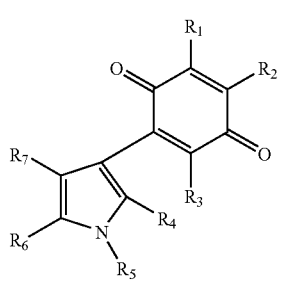

(I)

wherein:

$R_1$ and $R_3$ are each independently hydrogen, OH, SH, halo, amino, alkoxy, aminoalkyl, alkyl, aryl, acyloxy, or (acyloxy)alkyl;

$R_2$ is hydrogen, aryl, heteroaryl, indolyl, alkyl, alkoxy, phenoxy, anilino, amino, halo, acyloxy, or (acyloxy)alkyl;

or $R_1$ and $R_2$ together form an aromatic ring (e.g., R1 and R2 together form —CH═CH—CH—, —CH═CH—CH═CH—, or —CH═CH—CH═CH—CH═CH—);

$R_5$ is hydrogen, $C_1$–$C_7$ alkyl, $C_2$–$C_7$ alkenyl, $C_2$–$C_7$ alkynyl, arylalkyl, or aryl;

$R_4$ is hydrogen, branched or unbranched saturated $C_1$–$C_n$ alkyl, branched or unbranched unsaturated $C_1$–$C_n$ alkyl, alkylcarboxy, $C_2$–$C_m$ alkenyl, alkynyl, alkenylcarboxy, aryl, alkylaryl hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 2–7 or 12, and m is an integer from 3–7 or 12; and $R_6$ and $R_7$ are each independently hydrogen, cycloalkyl, alkyl, alkoxy, halo, aryl, heteroaryl, phenoxy, anilino, amino, or form part of an aromatic ring (e.g., R6 and R7 together form —CH═CH—CH═CH—, —CH═CH—CH═CH—, or —CH═CH—CH═CH—CH═CH—) wherein said aromatic ring is unsubstituted or substituted 1, 2 or 3 times with cycloalkyl, alkyl, alkoxy, halo, aryl, heteroaryl, phenoxy, anilino, or amino.

A further aspect of the present invention is a compound of the formula V:

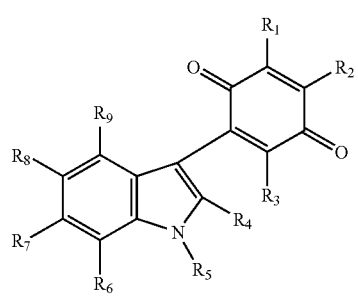

(V)

wherein:

$R_1$ and $R_3$ are each independently OH, SH, halo, amino, alkoxy, aminoalkyl, hydrogen, alkyl, aryl, acyloxy, or (acyloxy)alkyl;

$R_2$ is hydrogen, aryl, heteroaryl, indolyl, alkyl, alkoxy, phenoxy, anilino, amino, halo, acyloxy, or (acyloxy)alkyl;

$R_1$ and $R_2$ can constitute part of an aromatic ring (e.g., R1 and R2 together form —CH═CH—CH—, —CH═CH—CH═CH—, or —CH═CH—CH═CH—CH═CH—).

$R_5$ is hydrogen, $C_1$–$C_7$ alkyl, $C_2$–$C_7$ alkenyl, $C_2$–$C_7$ alkynyl, arylalkyl, or aryl; and $R_4$ and $R_6$–$R_9$ are each independently hydrogen, branched or unbranched $C_1$–$C_n$ alkyl, alkylcarboxy, $C_2$–$C_m$ alkenyl, alkynyl, alkenylcarboxy, aryl, alkylaryl, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 2 to 7 or 12, and m is an integer from 3 to 7 or 12.

A further aspect of the present invention is a method of treating a proliferative disease in a subject in need thereof, comprising administering to said subject, in an amount effective to treat said proliferative disease, a compound of formula I or V as given above. Examples of such said proliferative diseases include but are not limited to ovarian cancer, breast cancer, colon cancer, gastric carcinomas, non-small cell lung cancer, and non-Hodgkin's lymphoma.

A still further aspect of the present invention is a method for treating a viral infection in a subject so afflicted, said method comprising administering to the subject a compound of the formula I or V as given above in an amount effective to treat the viral disease. Examples of infections which may be treated include Poxviridae, Filoviridae, Herpesviridae, Hepadnaviridae, and Retroviridae infections.

A still further aspect of the present invention is a method for treating a neurodegenerative disease in a subject so afflicted, said method comprising administering to the subject a compound of the formula I or V as given above in an amount effective to treat said neurodegenerative disease. Examples of neurodegenerative diseases which may be so treated include but are not limited to Alzheimer's disease, Parkinson's disease, multiple sclerosis, and amyotropic lateral sclerosis.

A still further aspect of the present invention is the use of a compound of Formula I or Formula V (an active agent) as described above for the preparation of a medicament for the treatment of a disorder as described above.

The present invention is explained in greater detail in the specification set forth below.

DETAILED DESCRIPTION OF THE PREFERRED EMBODIMENTS

The term "treat" as used herein refers to any type of treatment that imparts a benefit to a patient afflicted with a disease, including improvement in the condition of the patient (e.g., in one or more symptoms), delay in the progression of the disease, etc.

The term "aryl" refers to an aromatic group or substituent whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$), naphthyl ($C_{10}H_7$), etc. Aryl groups may be unsubstituted or substituted one, two, three or more times with additional substituents as described below (e.g., alkyl, halo, alkoxy, etc.).

"Heteroaryl" means an unsubstituted or substituted 5- or 6-membered monocyclic hetereoaromatic ring or a 9- or 10-membered bicyclic hetereoaromatic ring containing 1, 2, 3 or 4 hetereoatoms which are independently N, S or O. Examples of hetereoaryl rings are furan, thiophene, pyrrole, pyridine, benzimidazole, indole, imidazole, isoquinoline, quinzoline and the like, the corresponding functional groups of which are al examples of heteroaryl groups that may be used in the present invention. Substituents on heteroaryl groups include those other as defined herein are included in the definition of heteroaryl.

"Alkyl" as used herein refers to a paraffinic hydrocarbon group which may be derived from an alkane by dropping one hydrogen from the formula. Examples are methyl, ethyl, propyl, isopropyl, butyl, tert-butyl, etc. Unless otherwise specified herein, "alkyl" as used herein is preferably a loweralkyl, e.g., C1–C4 loweralkyl. "Alkyl" groups as used herein may be saturated or unsaturated, although the unsaturated alkyls may be identified as "alkenyl" or "alkynyl" groups as described below.

"Cycloalkyl" as used herein means an unsubstituted or substituted 3- to 7-membered carbacyclic ring, which may be unsubstituted or substituted (e.g., from 3 to 7 times) with substituents as described herein.

"Alkenyl" as used herein refers to an alkyl group as defined above modified to contain at least one double bond (e.g., at least one degree of unsaturation). Unless otherwise specified herein, "alkenyl" as used herein is preferably a loweralkenyl, e.g., C1–C4 loweralkenyl.

"Alkynyl" as used herein refers to an alkyl group as defined above modified to contain at least one triple bond. Unless otherwise specified herein, "alkynyl" as used herein is preferably a loweralkynyl, e.g., C1–C4 loweralkynyl.

"Alkoxy" as used herein means a substituent of the formula —OR, where R is alkyl as defined above.

"Halo" as used herein refers to one of the electronegative elements of group VIIA of the periodic table (e.g., fluoro, chloro bromo, iodo).

"Amino" refers to the —NH$_2$ group.

"Aminoalkyl" refers to a group of the formula —NRR', where at least one, or both, of R and R' are alkyl as defined above. One of R and R' may optionally be H.

"Acyl" refers to an organic acid group in which the OH of the carboxyl group is removed so that a bond may be formed. Thus an acyl group may be generally represented by the formula RCO—, where R is a substituent as described herein (e.g., alkyl, aryl, arylalkyl), O is double bonded to the carbon, and the bond drawn in the structure is to the carbon shown in the structure). Examples include, but are not limited to acetyl, benzoyl, etc.

"Acyloxy" as used herein refers to a group of the formula —OR', where R' is acyl as defined above.

"(Acyloxy)alkyl" as used herein refers to a group of the formula —R—OR', where R' is acyl as defined above and R is alkyl as defined above.

"Arylalkyl" as used herein refers to a group of the formula —RR", where R" is aryl as defined above and R is alkyl as defined above. An example is benzyl.

The term "pharmaceutically acceptable" as used herein means that the compound or composition is suitable for administration to a subject to achieve the treatments described herein, without unduly deleterious side effects in light of the severity of the disease and necessity of the treatment.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes.

1. Active Compounds

The methods of the present invention include the administration of compounds of Formula I, while pharmaceutical compositions of the present invention comprise compounds of Formula I as described above.

Compounds illustrative of the compounds of Formula (I) above include:

2-tert-Butyl-3,6-dihydroxy-5-(5-phenethyl-4-phenyl-1H-pyrrol-3-yl)-[1,4]benzoquinone;

Acetic acid 4-acetoxymethoxy-2-(5-benzyloxymethyl-4-methyl-1H-pyrrol-3-yl)-3,6-dioxo-5-phenyl-cyclohexa-1,4-dienyloxymethyl ester; and Acetic acid 4-acetoxy-2-(2-cyclopropyl-4,5,6,7-tetrahydro-1H-indol-3-yl)-5-methyl-3,6-dioxo-cyclohexa-1,4-dienyl ester.

The methods of the present invention include the administration of compounds of Formula V, while pharmaceutical compositions of the present invention comprise compounds of Formula V as given above. Compounds illustrative of the compounds of Formula (V) above include: 2,5-Dichloro-3-(1H-indol-3-yl)-[1,4]benzoquinone; 2,5-Dichloro-3-(2-metthyl-1H-indol-3-yl)-[1,4]benzoquinone; 2,5-Dichloro-3-(2,5dimethyl-1H-indol-3-yl)-[1,4]benzoquinone; 2,5-Dichloro-3-(5-methoxy-2-methyl-1H-indol-3-yl)-[1,4]benzoquinone; 2,5-Dichloro-3-(5-chloro-2-methyl-1H-indol-3-yl)-[1,4]benzoquinone; 2,5-Dichloro-3-(2-cyclopropyl-1H-indol-3-yl)-[1,4]benzoquinone; 2,5-Dichloro-3-(2-phenyl-1H-indol-3-yl)-[1,4]benzoquinone; 2,5-Dichloro-3-(1-methyl-1H-indol-3-yl)-[1,4]benzoquinone; 2,5-Dichloro-3-(2-ethyl-1H-indol-3-yl)-[1,4]benzoquinone; 2,5-Dichloro-3-(2-isopropyl-1H-indol-3-yl)-[1,4]benzoquinone; 2,5-Dichloro-3-(2-tert-butyl-1H-indol-3-yl)-[1,4]benzoquinone; 2,5-Dichloro-3-[2-(1-methyl-cyclopropyl)-1H-indol-3-yl]-[1,4]benzoquinone; 2,5-Dichloro-3-[2-(1-methyl-cyclohexyl)-1H-indol-3-yl]-[1,4]benzoquinone; 3-(4-Fluoro-1H-indol-3-yl)-2,5-dichloro-[1,4]benzoquinone; 3-(4-Chloro-1H-indol-3-yl)-2,5-dichloro-[1,4]benzoquinone; 3-(4-Bromo-1H-indol-3-yl)-2,5-dichloro-[1,4]benzoquinone; 2,5-Dichloro-3-(4-methoxy-1H-indol-3-yl)-[1,4]benzoquinone; 3-(4-Benzyloxy-1H-indol-3-yl)-2,5-dichloro-[1,4]benzoquinone; 2,5-dichloro-3-(4-methyl-1H-indol-3-yl)-[1,4]benzoquinone; 3-(5-Fluoro-1H-indol-3-yl)-2,5-dichloro-[1,4]benzoquinone; 3-(5-Chloro-1H-indol-3-yl)-2,5-dichloro-[1,4]benzoquinone; 3-(5-Bromo-1H-indol-3-yl)-2,5-dichloro-[1,4]benzoquinone; 2,5-Dichloro-3-(5-hydroxy-1H-indol-3-yl)-[1,4]benzoquinone; 2,5-Dichloro-3-(5-methoxy-1H-indol-3-yl)-[1,4]benzoquinone; 3-(5-Benzyloxy-1H-indol-3-yl)-2,5-dichloro-[1,4]benzoquinone; 2,5-Dichloro-3-(5-methyl-1H-indol-3-yl)-[1,4]benzoquinone; 3-(6-Fluoro-1H-indol-3-yl)-2,5-dichloro-[1,4]benzoquinone; 3-(6-Chloro-1H-indol-3-yl)-2,5-dichloro-[1,4]benzoquinone; 3-(6-Bromo-1H-indol-3-yl)-2,5-dichloro-[1,4]benzoquinone; 2,5-Dichloro-3-(6-methyl-1H-indol-3-yl)-[1,4]benzoquinone; 2,5-Dichloro-3-(7-propyl-1H-indol-3-yl)-[1,4]benzoquinone; 2,5-Dichloro-3-(7-methyl-1H-indol-3-yl)-[1,4]benzoquinone; 3-(7-tert-butyl-1H-indol-3-yl)-2,5-dichloro-[1,4]benzoquinone; 2,5-Dichloro-3-(7-phenyl-1H-indol-3-yl)-[1,4]benzoquinone; 2,5-Dichloro-3-(7-methoxy-1H-indol-3-yl)-[1,4]benzoquinone; 3-(7-Benzyloxy-1H-indol-3-yl)-2,5-dichloro-[1,4]benzoquinone; 3-(7-Fluoro-1H-indol-3-yl)-2,5-dichloro-[1,4]benzoquinone; 3-(7-Chloro-1H-indol-3-yl)-2,5-dichloro-[1,4]benzoquinone; 3-(7-Bromo-1H-indol-3-yl)-2,5- dichloro-[1,4]benzoquinone; 3-(7-Benzyl-1H-indol-3-yl)-2, 5-dichloro-[1,4]benzoquinone; 2,5-Dichloro-3-[7-(2-methyl-benzyl)-1H-indol-3-yl]-[1,4]benzoquinone; 3-(1H-Benzo[g]indol-3-yl)-2,5-dichloro-[1,4]benzoquinone; 3-(2,6-Dimethyl-1H-indol-3-yl)-2,5-dichloro-[1,4] benzoquinone; 3-(2,7-Dimethyl-1H-indol-3-yl)-2,5-dichloro-[1,4]benzoquinone; 3-(6,7-Dimethyl-1H-indol-3-yl)-2,5-dichloro-[1,4]benzoquinone; 3-(5,6-Methylenedioxy-1H-indol-3-yl)-2,5-dichloro-[1,4] benzoquinone; 3-(5,6-Dimethoxy-1H-indol-3-yl)-2,5-dichloro-[1,4]benzoquinone; 2,5-Dihydroxy-3-(1H-indol-3-yl)-[1,4]benzoquinone; 2,5-Dihydroxy-3-(2-metthyl-1H-indol-3-yl)-[1,4]benzoquinone; 2,5-Dihydroxy-3-(2,5dimethyl-1H-indol-3-yl)-[1,4]benzoquinone; 2,5-Dihydroxy-3-(5-methoxy-2-methyl-1H-indol-3-yl)-[1,4] benzoquinone; 2,5-Dihydroxy-3-(5-chloro-2-methyl-1H-indol-3-yl)-[1,4]benzoquinone; 2,5-Dihydroxy-3-(2-cyclopropyl-1H-indol-3-yl)-[1,4]benzoquinone; 2,5-Dihydroxy-3-(2-phenyl-1H-indol-3-yl)-[1,4]benzoquinone; 2,5-Dihydroxy-3-(1-methyl-1H-indol-3-yl)-[1,4]benzoquinone; 2,5-Dihydroxy-3-(2-ethyl-1H-indol-3-yl)-[1,4] benzoquinone; 2,5-Dihydroxy-3-(2-isopropyl-1H-indol-3-yl)-[1,4]benzoquinone; 2,5-Dihydroxy-3-(2-tert-butyl-1H-indol-3-yl)-[1,4]benzoquinone; 2,5-Dihydroxy-3-[2-(1-methyl-cyclopropyl)-1H-indol-3-yl]-[1,4]benzoquinone; 2,5-Dihydroxy-3-[2-(1-methyl-cyclohexyl)-1H-indol-3-yl]-[1,4]benzoquinone; 3-(4-Fluoro-1H-indol-3-yl)-2,5-dihydroxy-[1,4]benzoquinone; 3-(4-Chloro-1H-indol-3-yl)-2,5-dihydroxy-[1,4]benzoquinone; 3-(4-Bromo-1H-indol-3-yl)-2,5-dihydroxy-[1,4]benzoquinone; 2,5-Dihydroxy-3-(4-methoxy-1H-indol-3-yl)-[1,4]benzoquinone; 3-(4-Benzyloxy-1H-indol-3-yl)-2,5-dihydroxy-[1,4] benzoquinone; 2,5-dihydroxy-3-(4-methyl-1H-indol-3-yl)-[1,4]benzoquinone; 3-(5-Fluoro-1H-indol-3-yl)-2,5-dihydroxy-[1,4]benzoquinone; 3-(5-Chloro-1H-indol-3-yl)-2,5-dihydroxy-[1,4]benzoquinone; 3-(5-Bromo-1H-indol-3-yl)-2,5-dihydroxy-[1,4]benzoquinone; 2,5-Dihydroxy-3-(5-hydroxy-1H-indol-3-yl)-[1,4]benzoquinone; 2,5-Dihydroxy-3-(5-methoxy-1H-indol-3-yl)-[1,4] benzoquinone; 3-(5-Benzyloxy-1H-indol-3-yl)-2,5-dihydroxy-[1,4]benzoquinone; 2,5-Dihydroxy-3-(5-methyl-1H-indol-3-yl)-[1,4]benzoquinone; 3-(6-Fluoro-1H-indol-3-yl)-2,5-dihydroxy-[1,4]benzoquinone; 3-(6-Chloro-1H-indol-3-yl)-2,5-dihydroxy-[1,4]benzoquinone; 3-(6-Bromo-1H-indol-3-yl)-2,5-dihydroxy-[1,4]benzoquinone; 2,5-Dihydroxy-3-(6-methyl-1H-indol-3-yl)-[1,4]benzoquinone; 2,5-Dihydroxy-3-(7-propyl-1H-indol-3-yl)-[1,4]benzoquinone; 2,5-Dihydroxy-3-(7-methyl-1H-indol-3-yl)-[1,4]benzoquinone; 3-(7-tert-butyl-1H-indol-3-yl)-2,5-dihydroxy-[1,4]benzoquinone 2,5-Dihydroxy-3-(7-phenyl-1H-indol-3-yl)-[1,4]benzoquinone; 2,5-Dihydroxy-3-(7-methoxy-1H-indol-3-yl)-[1,4]benzoquinone; 3-(7-Benzyloxy-1H-indol-3-yl)-2,5-dihydroxy-[1,4] benzoquinone; 3-(7-Fluoro-1H-indol-3-yl)-2,5-dihydroxy-[1,4]benzoquinone; 3-(7-Chloro-1H-indol-3-yl)-2,5-dihydroxy-[1,4]benzoquinone; 3-(7-Bromo-1H-indol-3-yl)-2,5-dihydroxy-[1,4]benzoquinone; 3-(7-Benzyl-1H-indol-3-yl)-2,5-dichloro-[1,4]benzoquinone; 2,5-Dihydroxy-3-[7-(2-methyl-benzyl)-1H-indol-3-yl]-[1,4]benzoquinone; 3-(1H-Benzo[g]indol-3-yl)-2,5-dihydroxy-[1,4]benzoquinone; 3-(2,6-Dimethyl-1H-indol-3-yl)-2,5-dihydroxy-[1,4]benzoquinone; 3-(2,7-Dimethyl-1H-indol-3-yl)-2,5-dihydroxy-[1,4]benzoquinone; 3-(6,7-Dimethyl-1H-indol-3-yl)-2,5-dihydroxy-[1,4]benzoquinone; 3-(5,6-Methylenedioxy-1H-indol-3-yl)-2,5-dihydroxy-[1,4]benzoquinone; and 3-(5,6-Dimethoxy-1H-indol-3-yl)-2,5-dihydroxy-[1,4]benzoquinone.

The active compounds disclosed herein can, as noted above, be prepared in the form of their pharmaceutically acceptable salts. Pharmaceutically acceptable salts are salts that retain the desired biological activity of the parent compound and do not impart undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; (b) salts formed from elemental anions such as chlorine, bromine, and iodine, and (c) salts derived from bases, such as ammonium salts, alkali metal salts such as those of sodium and potassium, alkaline earth metal salts such as those of calcium and magnesium, and salts with organic bases such as dicyclohexylamine and N-methyl-D-glucamine.

2. Pharmaceutical Formulations

The active compounds described above may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active compound (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active compound. One or more active compounds may be incorporated in the formulations of the invention, which may be prepared by any of the well known techniques of pharmacy consisting essentially of admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Preferred routes of parenteral administration include intrathecal injection, including directly into the tumor, and intraventricular injection into a ventricle of the brain.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Formulations suitable for buccal (sub-lingual) administration include lozenges comprising the active compound in a flavoured base, usually sucrose and acacia or tragacanth; and pastilles comprising the compound in an inert base such as gelatin and glycerin or sucrose and acacia.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes which render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising a compound of Formula (I), or a salt thereof, in a unit dosage form in a sealed container. The compound or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the compound or salt. When the compound or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Formulations suitable for rectal administration are preferably presented as unit dose suppositories. These may be prepared by admixing the active compound with one or more conventional solid carriers, for example, cocoa butter, and then shaping the resulting mixture.

Formulations suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Formulations suitable for transdermal administration may be presented as discrete patches adapted to remain in intimate contact with the epidermis of the recipient for a prolonged period of time. Formulations suitable for transdermal administration may also be delivered by iontophoresis (see, for example, *Pharmaceutical Research* 3 (6):318 (1986)) and typically take the form of an optionally buffered aqueous solution of the active compound. Suitable formulations comprise citrate or bis\tris buffer (pH 6) or ethanol/water and contain from 0.1 to 0.2M active ingredient.

Further, the present invention provides liposomal formulations of the compounds disclosed herein and salts thereof. The technology for forming liposomal suspensions is well known in the art. When the compound or salt thereof is an aqueous-soluble salt, using conventional liposome technology, the same may be incorporated into lipid vesicles. In such an instance, due to the water solubility of the compound or salt, the compound or salt will be substantially entrained within the hydrophilic center or core of the liposomes. The lipid layer employed may be of any conventional composition and may either contain cholesterol or may be cholesterol-free. When the compound or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

Of course, the liposomal formulations containing the compounds disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble compounds disclosed herein, or salts thereof, such as aqueous base emulsions. In such an instance, the composition will contain a sufficient amount of pharmaceutically acceptable emulsifying agent to emulsify the desired amount of the compound or salt thereof. Particularly useful emulsifying agents include phosphatidyl cholines, and lecithin.

In addition to compounds of formula (I) or (V) or their salts, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well known in the art.

3. Dosage and Routes of Administration

As noted above, the present invention provides pharmaceutical formulations comprising the active compounds (including the pharmaceutically acceptable salts thereof), in pharmaceutically acceptable carriers for oral, rectal, topical, buccal, parenteral, intramuscular, intradermal, or intravenous, and transdermal administration.

Preferred routes of parenteral administration include intrathecal injection, including directly into the tumor, and intraventricular injection into a ventricle of the brain.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

The therapeutically effective dosage of any specific compound, the use of which is in the scope of present invention, will vary somewhat from compound to compound, and patient to patient, and will depend upon the condition of the patient and the route of delivery. As a general proposition, a dosage from about 0.1 to about 50 mg/kg will have therapeutic efficacy, with all weights being calculated based upon the weight of the active compound, including the cases where a salt is employed. Toxicity concerns at the higher level may restrict intravenous dosages to a lower level such as up to about 10 mg/kg, with all weights being calculated based upon the weight of the active base, including the cases where a salt is employed. A dosage from about 10 mg/kg to about 50 mg/kg may be employed for oral administration. Typically, a dosage from about 0.5 mg/kg to 5 mg/kg may be employed for intramuscular injection. Preferred dosages are 1 µmol/kg to 50 µmol/kg, and more preferably 22 µmol/kg and 33 µmol/kg of the compound for intravenous or oral administration. The duration of the treatment is usually once per day for a period of two to three weeks or until the condition is essentially controlled. Lower doses given less frequently can be used prophylactically to prevent or reduce the incidence of recurrence of the infection.

4. Compounds as Antiviral Agents

There are comparatively fewer antivirals than there are antibiotics. Since viruses engage in much of their infective activity by hijacking a cell's machinery and essentially directing the cell to manufacture virus particles, agents with antiviral effect may additionally inhibit cellular functions in non-infected cells. For example, iododeoxyuridine, one of the first antiviral agents, has significant systemic toxicity.

While advances have lead to more advanced compounds, such as acyclovir and AZT, the number of viruses that are currently targeted by antiviral medicine lags far behind that of antibiotics.

The present invention shows use in several families of viruses, both in traditional antiviral targets and in families that are currently unmet with antiviral medication.

In one embodiment of the invention, compounds of the invention are effective in treating infection by viruses of the family Poxviridae, such as variola (smallpox), vaccinia, goatpox, swinepox. Examples of such compounds include but are not limited to compounds 6C, 6F, 11C, and 8H from Table 3 below.

It is known in the art that asterriquinone may inhibit HIV replication by interacting with viral Reverse Transcriptase. In another embodiment of the invention, compounds of the invention are effective in treating infection by viruses which utilize a Reverse Transcriptase mechanism, namely viruses of the family Retroviridae. Examples of such compounds include but are not limited to the compounds listed in Table 3 below.

Filoviridae infections are characterized by a rapidly acute and often fatal infection in a large percentage of patients. Additionally, Filoviridae, specifically Ebola, are feared biological weapons agents. Compounds embodying this invention may have utility against Filoviridae, such as Ebola and Marburg.

Hepadnaviridae exhibit control over the RAS pathway by utilization of viral protein X. Compounds embodying this invention may have utility against Hepadnaviridae, such as Hepatitis B.

Herpesviridae depend on a viral thymadine kinase pathway, the target of antivirals such as acyclovir. Compounds embodying this invention may have utility against Herpesviridae, such as HSV-1.

The present invention is explained in greater detail in the following non-limiting Examples.

EXAMPLE 1

HCl Preparation of 2,5-dichloro-3-(2-methyl-1H-indol-3-yl)-[1,4]benzoquinone (Procedure A)

To a solution of 2-methylindole (0.500 g, 3.81 mmol) in THF (30 mL) was added 2,5-dichloro-1,4-benzoquinone (1.35 g, 7.62 mmol) at room temperature. To this mixture was added concentrated HCl (12 N, 0.38 mL, 4.57 mmol) dropwise. After the reaction mixture was stirred for 5 hours (5 h–12 h) at room temperature, DDQ (1.73 g, 7.62 mmol) was added. After stirring for 3 hours (3 h–12 h) at room temperature, the mixture was diluted with EtOAc (100 mL). The organic solution was washed with saturated NaHCO$_3$ (3×100 mL) and brine (100 mL), and dried over Na$_2$SO$_4$. The residue was concentrated and purified by flash column chromatography using 15% EtOAc in hexane as eluent to afford pure 2,5-dichloro-3-(2-methyl-1H-indol-3-yl)-[1,4]benzoquinone (1.13 g, 97%) as a blue solid. Melting point 158–159° C. R$_f$=0.35 (3:7, EtOAc/hexane). $^1$H NMR (CDCl$_3$) δ 8.40 (bs, NH), 7.24–7.11 (m, 5H), 2.26 (s, 3H). $^1$H NMR (d$_6$-acetone): δ 10.60 (1H, br s), 7.39 (1H, s), 7.36 (1H, d, J=7.8 Hz), 7.24 (1H, d, J=7.8 Hz), 7.10 (1H, t, J=7.8 Hz), 7.01 (1H, t, J=7.8 Hz). $^{13}$C NMR (CDCl$_3$) δ 177.7, 176.6, 144.3, 139.8, 139.3, 136.9, 135.1, 133.1, 126.6, 122.0, 120.5, 119.6, 110.8, 104.8, 13.9. IR (KBr): 3388, 3061, 1676, 1566, 1459, 1250, 1032, 749 cm$^{-1}$. Anal. Calcd. for C$_{15}$H$_9$Cl$_2$NO$_2$: C, 58.85; H, 2.96; Cl, 23.16; N, 4.58. Found: C, 58.85; H, 2.96; Cl, 23.16; N, 4.58. HRMS (EI) Calcd. For C$_{15}$H$_9$Cl$_2$NO$_2$ [M$^+$]: 305.0010. Found: 305.0002.

EXAMPLE 2

H$_2$SO$_4$ Preparation of 2,5-dichloro-3-(5-methoxy-1H-indol-3-yl)-[1,4]benzoquinone (Procedure B)

To a solution of 2,5-dichloro-1,4-benzoquinone (0.242 g, 1.37 mmol) in THF (3 mL) was added H$_2$SO$_4$ (35 µL, 0.68 mmol) at room temperature. To this mixture was added 5-methoxyindole (0.100 g, 0.68 mmol). After the reaction mixture was stirred for 1 hour at room temperature under nitrogen protection, DDQ (0.232 g, 1.02 mmol) was added. After stirring for 2 hours, the mixture was diluted with ethyl acetate (100 mL). The organic layer was washed with sat. NaHCO$_3$ (3×20 mL) and brine (20 mL), and dried over Na$_2$SO$_4$. The solution was concentrated and purified by flash column chromatography using 15% EtOAc in hexane as eluent to afford 2,5-dichloro-3-(5-methoxy-1H-indole-3-yl)-[1,4]benzoquinone (0.211 g, 96%) as blue needles from benzene/hexane. Melting Point 195–196° C. $^1$H NMR (CDCl$_3$): 6.78 (1H, d, J=2.4 Hz), 6.93 (1H, dd, J=2.1, 8.4 Hz), 7.23 (1H, s), 7.34 (1H, d, J=9.0 Hz), 7.54 (1H, d, J=3.0 Hz), 8.62 (1H, br s). $^{13}$C NMR (d$_6$-acetone): 55.2, 103.8, 106.7, 112.4, 112.8, 126.5, 130.9, 131.0, 131.4, 133.4, 139.8, 143.7, 154.8, 177.8, 178.0. IR (KBr): 3328, 3043, 2924, 2855, 1675, 1638, 1543, 1484, 1260, 1227 cm$^{-1}$. Anal. Calcd. for C$_{15}$H$_9$Cl$_2$NO$_3$: C, 55.93; H, 2.82; N, 4.35. Found: C, 55.72; H, 2.99; N, 4.24.

EXAMPLE 3

AcOH Preperation of 2,5-dichloro-3-[2-(1-methyl-cyclopropyl)-1H-indol-3-yl]-[1,4]benzoquinone (Procedure C)

To a solution of 2,5-dichloro-1,4-benzoquinone (0.177 g, 1.00 mmol) in AcOH (2 mL) was added 2-(1methyl-cyclopropyl)indole (0.081 g, 0.47 mmol). After the reaction mixture was stirred for 2 h at 50° C. under nitrogen protection, Ag$_2$CO$_3$ on Celite® (50%, 0.500 g, 0.90 mmol)

was added. After stirring for 4 h at room temperature, the solution was diluted with ethyl acetate (100 mL). The organic layer was washed with sat. NaHCO$_3$ (3×20 mL) and brine (20 mL), and dried over Na$_2$SO$_4$. The solution was concentrated and purified by flash column chromatography using 15% EtOAc in hexane as eluent to afford 2,5-dichloro-3-[2-(1-methyl-cyclopropyl)-1H-indol-3-yl]-[1,4]benzoquinone (0.148 g, 90%) as blue needles from benzene/hexane. Melting Point 170–171° C. $^1$H NMR (d$_6$-acetone): 0.53–0.60 (1H, m), 0.64–0.70 (1H, m), 0.70–0.77 (1H, m), 0.92–0.98 (1H, m), 1.48 (3H, s), 7.01 (1H, dt, J=1.2, 7.5 Hz), 7.10 (1H, dt, J=1.2, 7.5 Hz), 7.24 (1H, dd, J=0.6, 7.2 Hz), 7.37 (1H, d, J=7.8 Hz), 7.39 (1H, s), 10.70 (1H, s). $^{13}$C NMR (d$_6$-acetone): 13.3, 14.1, 15.1, 24.5, 103.6, 111.4, 119.7, 119.9, 121.9, 126.8, 133.8, 136.0, 140.4, 140.8, 143.9, 144.0, 177.1, 177.9. IR (KBr): 3409, 3059, 3004, 2966, 2927, 1662, 1620, 1567, 1435, 1270, 1241, 1028, 755 cm$^{-1}$. Anal. Calcd. for C$_{18}$H$_{13}$Cl$_2$NO$_2$: C, 62.45; H, 3.78; N, 4.05. Found: C, 62.30; H, 3.77; N, 3.94.

EXAMPLE 4

Hydrolysis of 2,5-dichloro-3-[2-(1-methyl-cyclopropyl)-1H-indol-3-yl]-[1,4]benzoquinone (Procedure D)

To a refluxing solution of 2,5-dichloro-3-[2-(1-methyl-cyclopropyl)-1H-indole-3-yl]-[1,4]benzoquinone (0.056 g, 0.16 mmol) in MeOH (6 mL) was added 10% aqueous NaOH (3 mL) dropwise. After refluxing for a half hour, the mixture was poured into cold water (20 mL). H$_2$SO$_4$ (10%) was added to acidify the mixture, which was extracted with EtOAc (3×10 mL). The organic layer was washed with brine (10 mL) and dried over Na$_2$SO$_4$. The solution was concentrated and purified by flash column chromatography (oxalic acid-coated silica gel) using 30% EtOAc in hexane as the eluent to afford 2,5-dihydroxy-3-[2-(1-methyl-cyclopropyl)-1H-indol-3-yl]-[1,4]benzoquinone (0.044 g, 87%) as dark blue needles from acetone/hexane. Melting Point 103° C. (dec). $^1$H NMR (d$_6$-acetone): 0.55–0.62 (2H, m), 0.81–0.87 (2H, m), 1.45 (3H, s), 6.08 (1H, s), 6.93 (1H, dt, J=0.9, 8.1 Hz), 7.04 (1H, dt, J=1.2, 8.1 Hz), 7.22 (1H, d, J=7.8 Hz), 7.31 (1H, dd, J=0.9, 8.1 Hz), 9.0–10.1 (2H, br s), 10.34 (1H, br s). $^{13}$C NMR (d$_6$-acetone): 13.3, 14.8, 24.4, 101.4, 103.6, 110.8, 112.3, 119.0, 119.5, 121.1, 128.4, 135.8, 142.2. IR (KBr): 3300, 3077, 2958, 2924, 1640, 1360, 1190, 746 cm$^{-1}$. HRMS (EI): calculated for C$_{18}$H$_{15}$NO$_4$ 309.1001; found 309.0999.

EXAMPLE 5

The following indoles were reacted according to the above procedures (procedures A–C, Examples 1–3) to achieve the listed yields and stated product.

TABLE 1

| Indole | Procedure A[a] | | Procedure B[b] | | Procedure C[b] | | End Product |
|---|---|---|---|---|---|---|---|
| indole | 70% | | | | 75% | 8 | 2,5-Dichloro-3-(1H-indol-3-yl)-[1,4]benzoquinone |
| 2-methylindole | 97% | | | | 96% | 2 | 2,5-Dichloro-3-(2-metthyl-1H-indol-3-yl)-[1,4]benzoquinone |
| 2,5-dimethylindole | 91% | | | | | | 2,5-Dichloro-3-(2,5dimethyl-1H-indol-3-yl)-[1,4]benzoquinone |
| 2-methyl-5-methoxyindole[c] | 89% | | | | | | 2,5-Dichloro-3-(5-methoxy-2-methyl-1H-indol-3-yl)-[1,4]benzoquinone |
| 2-methyl-5-chloroindole[c] | 75% | | | | | | 2,5-Dichloro-3-(5-chloro-2-methyl-1H-indol-3-yl)-[1,4]benzoquinone |
| 2-cyclopropylindole | 95% | | | | | | 2,5-Dichloro-3-(2-cyclopropyl-1H-indol-3-yl)-[1,4]benzoquinone |
| 2-phenylindole | 89% | | | | | | 2,5-Dichloro-3-(2-phenyl-1H-indol-3-yl)-[1,4]benzoquinone |
| N-methylindole | 87% | | | | | | 2,5-Dichloro-3-(1-methyl-1H-indol-3-yl)-[1,4]benzoquinone |
| 2-ethylindole | 95% | | | | | | 2,5-Dichloro-3-(2-ethyl-1H-indol-3-yl)-[1,4]benzoquinone |
| 2-isopropylindole | 70% | | | | | | 2,5-Dichloro-3-(2-isopropyl-1H-indol-3-yl)-[1,4]benzoquinone |
| 2-tert-butylindole | 54% | | | | 90% | 2 | 2,5-Dichloro-3-(2-tert-butyl-1H-indol-3-yl)-[1,4]benzoquinone |
| 2-(1-methylcyclopropyl)indole | | | 46% | 1 | 90% | 2 | 2,5-Dichloro-3-[2-(1-methyl-cyclopropyl)-1H-indol-3-yl]-[1,4]benzoquinone |
| 2-(1-methylcyclohexyl)indole | | | 50% | 24 | 91% | 10 | 2,5-Dichloro-3-[2-(1-methyl-cyclohexyl)-1H-indol-3-yl]-[1,4]benzoquinone |
| 4-fluoroindole | 0% | 120 | 16% | 42 | 14% | 22 | 3-(4-Fluoro-1H-indol-3-yl)-2,5-dichloro-[1,4]benzoquinone |
| 4-chloroindole | 0% | 120 | 54% | 92 | | | 3-(4-Chloro-1H-indol-3-yl)-2,5-dichloro-[1,4]benzoquinone |
| 4-bromoindole | 0% | 120 | 39% | 144 | | | 3-(4-Bromo-1H-indol-3-yl)-2,5-dichloro-[1,4]benzoquinone |
| 4-methoxyindole | | | 2% | 0.5 | 66% | 3 | 2,5-Dichloro-3-(4-methoxy-1H-indol-3-yl)-[1,4]benzoquinone |
| 4-benzyloxyindole | | | 1% | 0.5 | 65% | 3 | 3-(4-Benzyloxy-1H-indol-3-yl)-2,5-dichloro-[1,4]benzoquinone |

TABLE 1-continued

| Indole | Procedure A[a] | | Procedure B[b] | | Procedure C[b] | | End Product |
|---|---|---|---|---|---|---|---|
| 4-methylindole | | | 39% | 21 | 76% | 20 | 2,5-Dichloro-3-(4-methyl-1H-indol-3-yl)-[1,4]benzoquinone |
| 5-fluoroindole | | | 50% | 5 | 74% | 6 | 3-(5-Fluoro-1H-indol-3-yl)-2,5-dichloro-[1,4]benzoquinone |
| 5-chloroindole | | | 56% | 0.5 | 72% | 24 | 3-(5-Chloro-1H-indol-3-yl)-2,5-dichloro-[1,4]benzoquinone |
| 5-bromoindole | | | 57% | 0.5 | 73% | 24 | 3-(5-Bromo-1H-indol-3-yl)-2,5-dichloro-[1,4]benzoquinone |
| 5-hydroxyindole | | | 52% | 0.5 | 6% | 0.5 | 2,5-Dichloro-3-(5-hydroxy-1H-indol-3-yl)-[1,4]benzoquinone |
| 5-methoxyindole | | | 96% | 0.5 | | | 2,5-Dichloro-3-(5-methoxy-1H-indol-3-yl)-[1,4]benzoquinone |
| 5-benzyloxyindole | | | 92% | 0.5 | | | 3-(5-Benzyloxy-1H-indol-3-yl)-2,5-dichloro-[1,4]benzoquinone |
| 5-methylindole | | | 82% | 6 | 72% | 2 | 2,5-Dichloro-3-(5-methyl-1H-indol-3-yl)-[1,4]benzoquinone |
| 6-fluoroindole | | | 37% | 5 | 63% | 6 | 3-(6-Fluoro-1H-indol-3-yl)-2,5-dichloro-[1,4]benzoquinone |
| 6-chloroindole | | | 58% | 20 | 55% | 6 | 3-(6-Chloro-1H-indol-3-yl)-2,5-dichloro-[1,4]benzoquinone |
| 6-benzyloxyindole | | | 14% | 2 | 22% | 22 | 3-(6-Bromo-1H-indol-3-yl)-2,5-dichloro-[1,4]benzoquinone |
| 6-methylindole | | | 63% | 1 | 75% | 20 | 2,5-Dichloro-3-(6-methyl-1H-indol-3-yl)-[1,4]benzoquinone |
| 7-methylindole | 81% | | | | 83% | 22 | 2,5-Dichloro-3-(7-propyl-1H-indol-3-yl)-[1,4]benzoquinone |
| 7-propylindole | | | 82% | 6 | 81% | 5 | 2,5-Dichloro-3-(7-methyl-1H-indol-3-yl)-[1,4]benzoquinone |
| 7-tert-butylindole | | | 81% | 6 | 82% | 8 | 3-(7-tert-butyl-1H-indol-3-yl)-2,5-dichloro-[1,4]benzoquinone |
| 7-phenylindole | | | 66% | 12 | 66% | 4 | 2,5-Dichloro-3-(7-phenyl-1H-indol-3-yl)-[1,4]benzoquinone |
| 7-methoxyindole | 13% | 20 | 62% | 9 | 50% | 68 | 2,5-Dichloro-3-(7-methoxy-1H-indol-3-yl)-[1,4]benzoquinone |
| 7-benzyloxyindole | | | 71% | 5 | 65% | 6 | 3-(7-Benzyloxy-1H-indol-3-yl)-2,5-dichloro-[1,4]benzoquinone |
| 7-fluoroindole | | | | | 43 | 48 | 3-(7-Fluoro-1H-indol-3-yl)-2,5-dichloro-[1,4]benzoquinone |
| 7-chloroindole | | | 17 | 96 | 63 | 72 | 3-(7-Chloro-1H-indol-3-yl)-2,5-dichloro-[1,4]benzoquinone |
| 7-bromoindole | | | 34 | 72 | 41 | 48 | 3-(7-Bromo-1H-indol-3-yl)-2,5-dichloro-[1,4]benzoquinone |
| 7-benzylindole | | | 89 | 1 | | | 3-(7-Benzyl-1H-indol-3-yl)-2,5-dichloro-[1,4]benzoquinone |
| 7-o-methylbenzylindole | | | 88 | 1 | | | 2,5-Dichloro-3-[7-(2-methyl-benzyl)-1H-indol-3-yl]-[1,4]benzoquinone |
| 1H-Benzo[g]indole | | | 34% | 48 | | | 3-(1H-Benzo[g]indol-3-yl)-2,5-dichloro-[1,4]benzoquinone |
| 2,6-dimethylindole | | | | | 89% | 6 | 3-(2,6-Dimethyl-1H-indol-3-yl)-2,5-dichloro-[1,4]benzoquinone |
| 2,7-dimethylindole | | | 59% | 2 | 94% | 1 | 3-(2,7-Dimethyl-1H-indol-3-yl)-2,5-dichloro-[1,4]benzoquinone |
| 6,7-dimethylindole | | | 90% | 0.16 | 88% | 4 | 3-(6,7-Dimethyl-1H-indol-3-yl)-2,5-dichloro-[1,4]benzoquinone |
| 5,6-methylenedioxyindole | | | 10% | 2 | 10% | 2 | 3-(5,6-Methylenedioxy-1H-indol-3-yl)-2,5-dichloro-[1,4]benzoquinone |
| 5,6-dimethoxyindole | | | 9% | 24 | 33% | 0.5 | 3-(5,6-Dimethoxy-1H-indol-3-yl)-2,5-dichloro-[1,4]benzoquinone |

[a] variation from the standard reaction time (10 h) is given in the right column.
[b] time for consumption of indole using THF as solvent is given in the right column.
[c] used 0.3 eq HCl.

EXAMPLE 6

The mono-indolquinone starting products listed in Table 2 were reacted according procedure D (Example 4) to achieve the listed yields and stated end product. Also included in this example are characterizations of the starting and ending compounds.

TABLE 2

| Starting Product | Yield | End Product |
| --- | --- | --- |
| 2,5-Dichloro-3-(1H-indol-3-yl)-[1,4]benzoquinone mp 124–125° C. IR(KBr): 3362, 3062, 2922, 1666, 1645, 1559, 1248cm$^{-1}$. $^1$H NMR(CDCl$_3$): δ 7.19(1H, s), 7.20–7.28 (2H, m), 7.38(1H, m), 7.41(1H, m), 7.47(1H, d, J=3Hz), 8.94(1H, br s). $^{13}$C NMR(CDCl$_3$): δ 107.2, 112.0, 121.3, 122.0, 123.3, 125.3, 129.8, 133.4, 135.8, 137.4, 138.5, 144.3, 177.5, 178.0. HRMS (EI) Calcd. For C$_{14}$H$_7$Cl$_2$NO$_2$ [M$^+$]: 290.9854. Found: 290.9865. | 59% | 2,5-Dihydroxy-3-(1H-indol-3-yl)-[1,4]benzoquinone mp 219–220° C. IR(KBr): 3421, 3301, 1666, 1293, 1235, 931cm$^{-1}$. $^1$H NMR(d$_6$-acetone): δ 10.6(1H, br s), 9.0–10.0(2H, br), 7.59(1H, d, J=2.4Hz), 7.52 (1H, d, J=8.1Hz), 7.44(1H, d, J=8.1Hz), 7.11(1H, t, J=8.1Hz), 7.02(1H, t, J=8.1Hz), 6.01(1H, s); 13$_C$ NMR(d$_6$-acetone): δ 136.4, 127.6, 126.9, 121.9, 121.5, 119.2, 112.1, 111.5, 104.7, 103.2. HRMS (FAB) Calculated for C$_{14}$H$_9$NO$_4$ [M$^+$]: 255.0532. Found: 255.0529. |
| 2,5-Dichloro-3-(2-methyl-1H-indol-3-yl)-[1,4]benzoquinone The residue was concentrated and purified by flash column chromatography using 15% EtOAc in hexane as eluent to afford pure 2,5-dichloro-3-(2-methyl-1H-indol-3-yl)-[1,4]benzoquinone (1.13 g, 97%)as a blue solid. mp 158–159° C. R$_f$ =0.35(3:7, EtOAc/hexane). $^1$H NMR(CDCl$_3$)δ 8.40(bs, NH), 7.24–7.11(m, 5H), 2.26(s, 3H). $^1$H NMR (d$_6$-acetone): δ 10.60(1H, br s), 7.39(1H, s), 7.36(1H, d, J=7.8Hz), 7.24(1H, d, J=7.8Hz), 7.10(1H, t, J=7.8Hz), 7.01(1H, t, J=7.8Hz). $^{13}$C NMR(CDCl$_3$)δ 177.7, 176.6, 144.3, 139.8, 139.3, 136.9, 135.1, 133.1, 126.6, 122.0, 120.5, 119.6, 110.8, 104.8, 13.9. IR(KBr): 3388, 3061, 1676, 1566, 1459, 1250, 1032, 749cm$^{-1}$. Anal. Calcd. for C$_{15}$H$_9$Cl$_2$NO$_2$: C, 58.85; H, 2.96; Cl, 23.16; N, 4.58. Found: C, 58.85; H, 2.96; Cl, 23.16; N, 4.58. HRMS (EI) Calcd. For C$_{15}$H$_9$Cl$_2$NO$_2$ [M$^+$]: 305.0010. Found: 305.0002. | 62% | 2,5-Dihydroxy-3-(2-metthyl-1H-indol-3-yl)-[1,4]benzoquinone mp 222–223° C. IR(KBr): 3392, 3313, 1630, 1359, 1294, 1186cm$^{-1}$. $^1$H NMR(d$_6$-acetone): δ 10.27(1H, br s), 7.30(1H, d, J=8.1Hz), 7.23(1H, d, J=8.1Hz), 7.02(1H, t, J=8.1Hz), 6.94(1H, t, J=8.1Hz), 6.04(1H, s), 2.32(3H, s). $^{13}$C NMR(d$_6$-acetone): δ 136.0, 135.5, 128.6, 120.6, 119.8, 119.0, 111.9, 110.5, 103.4, 102.2, 12.8. HRMS (FAB) Calcd. For C$_{15}$H$_{11}$NO$_4$ [M$^+$]: 269.0688. Found: 269.0691. |
| 2,5-Dichloro-3-(2,5-dimethyl-1H-indol-3-yl)-[1,4]benzoquinone Blue crystals from benzene/hexane. mp 185–186° C. IR (KBr): 3346, 2922, 1671, 1656, 1559, 1259cm$^{-1}$. $^1$H NMR (CDCl$_3$): δ 2.32(3H, s), 2.41(3H, s), 6.94(1H, m), 6.97 (1H, m), 7.18(1H, dd, J=0.6, 8.4Hz), 7.21(1H, s), 8.19 (1H, br s). $^{13}$C NMR(CDCl$_3$): δ 14.3, 21.9, 104.8, 110.7, 119.8, 123.9, 127.2, 130.3, 133.4, 133.7, 137.1, 139.8, 140.1, 144.7, 177.0, 178.1. Anal. Calcd. for C$_{16}$H$_{11}$Cl$_2$NO$_2$: C, 60.02; H, 3.46; N, 4.37. Found: C, 59.80; H, 3.58; N, 4.43. | 73% | 2,5-Dihydroxy-3-(2,5dimethyl-1H-indol-3-yl)-[1,4]benzoquinone Green crystals from benzene/hexane. mp 231–232° C. IR(KBr): 3416, 3287, 2917, 2858, 1619, 1355, 1184cm$^{-1}$, $^1$H NMR(d$_6$-acetone): δ 10.12(1H, br s), 9.0–10.0(2H, br), 7.18(1H, d, J=8.1Hz), 7.01(1H, s), 6.85(1H, d, J=8.4Hz), 6.04(1H, s), 2.33(3H, s), 2.29(3H, s). $^{13}$C NMR(d$_6$-acetone): δ 135.5, 134.4, 128.8, 127.6, 122.1, 119.6, 110.2, 103.4, 101.7, 21.1, 12.8, HRMS (FAB) Calcd. For C$_{16}$H$_{13}$NO$_4$ [M$^+$]: 283.0845. Found: 283.0846. |
| 2,5-Dichloro-3-(5-methoxy-2-methyl-1H-indol-3-yl)-[1,4]benzoquinone Blue crystals from benzene/hexane. mp 199.2–199.5° C. IR (KBr): 3357, 2938, 2895, 2820, 1672, 1645, 1565, 1275, 1253cm$^{-1}$. $^1$H NMR(CDCl$_3$): δ 2.28(3H, s), 3.78(3H, s), 6.58(1H, d, J=2.4Hz), 6.80(1H, dd, J=2.4, 9Hz), 7.17 (1H, d, J=9Hz), 7.22(1H, s), 8.22(1H, br s). $^{13}$C NMR (CDCl$_3$): δ 14.4, 56.2, 102.5, 105.1, 111.8, 112.2, 127.5, 130.4, 133.4, 137.8, 139.7, 139.9, 144.7, 154.9, 176.9, 178.1. HRMS (EI) Calcd. For C$_{16}$H$_{11}$Cl$_2$NO$_2$ [M$^+$]: 335.0116. Found: 335.0123. | 81% | 2,5-Dihydroxy-3-(5-methoxy-2-methyl-1H-indol-3-yl)-[1,4]benzoquinone mp 212° C. (dec). IR (KBr): 3389, 3080, 2925, 1612, 1484, 1358, 1329, 1198, 799cm$^{-1}$. $^1$H NMR(d$_6$-acetone): δ 10.10(1H, br s), 9.0–9.8(2H, br), 7.16 (1H, d, J=6.6Hz), 6.75(1H, s), 6.65(1H, J=6.6Hz), 6.00(1H, s), 3.70(3H, s), 2.26(3H, s). $^{13}$C NMR(d$_6$-acetone): δ 154.1, 136.2, 131.0, 129.1, 112.0, 111.0, 110.4, 103.3, 102.3, 102.1, 55.1, 12.7. HRMS (FAB) Calculated for C$_{16}$H$_{13}$NO$_5$ [M$^+$]: 299.0794. Found: 299.0795. |
| 2,5-Dichloro-3-(5-chloro-2-methyl-1H-indol-3-yl)-[1,4]benzoquinone Blue crystals from benzene/hexane. mp 254–255° C. IR (KBr): 3336, 3078, 1678, 1656, 1570, 1275cm$^{-1}$. $^1$H NMR (d$_6$-acetone): δ 2.36(3H, s), 7.07(1H, dd, J=2.1, 8.7Hz), 7.30(1H, d, J=2.1Hz), 7.38(1H, dd, J=0.6, 8.7Hz), 7.39 (1H, s), 10.9(1H, br s). $^{13}$C NMR(d$_6$-acetone): δ 13.0, 104.7, 112.4, 119.1, 121.4, 125.1, 128.7, 133.4, 134.5, 139.1, 139.3, 140.5, 144.2, 176.9, 178.1. Calculated for C$_{15}$H$_8$Cl$_3$NO$_2$: C, 52.90; H, 2.37; N, 4.11; Found: C, 52.79; H, 2.44; N, 3.97. | 87% | 2,5-Dihydroxy-3-(5-chloro-2-methyl-1H-indol-3-yl)-[1,4]benzoquinone mp 230° C. (dec). IR(KBr): 3440, 3315, 1632, 1470, 1358, 1184, 795cm$^{-1}$. $^1$H NMR(d$_6$-acetone): δ 10.43 (1H, br s), 9.0–10.0(2H, br), 7.28(1H, d, J=6.3Hz), 7.23(1H, d, J=1.5Hz), 6.98(1H, dd, J=6.3, 1.5Hz), 6.00(1H, s), 2.29(3H, s). $^{13}$C NMR(d$_6$-acetone): δ 137.5, 134.5, 129.7, 124.3, 120.5, 119.2, 111.9, 111.0, 103.4, 12.6. HRMS (FAB) Calculated for C$_{17}$H$_{13}$NO$_4$ [M$^+$]: 303.0298. Found: 303.0302. |

TABLE 2-continued

| Starting Product | Yield | End Product |
|---|---|---|
| 2,5-Dichloro-3-(2-cyclopropyl-1H-indol-3-yl)-[1,4]benzoquinone<br>This compound was synthesized according to the general procedure A from 2-cyclopropyl-1H-indole (100 mg, 0.636 mmol) and 2,5-dichloro-1,4-benzoquinone (225 mg, 1.27 mmol) and obtained as a blue solid (200 mg, 95%). mp 181–182° C. $R_f$ =0.37(3:7, EtOAc/hexane). $^1$H NMR(CDCl$_3$): δ 8.32(1H, br s), 7.09–7.23(5H, m), 1.87(1H, m), 0.93(2H, m), 0.70(2H, m). $^{13}$C NMR(CDCl$_3$)δ 177.8, 176.4, 144.3, 141.9, 139.6(2C), 134.7, 133.0, 126.6, 122.1, 120.5, 119.5, 110.9, 105.3, 9.4, 7.3. IR(KBr): 3450, 3386, 3061, 1676, 1650, 1561, 1448, 1273, 1241, 1032, 882, 745cm$^{-1}$. Anal. Calcd. for C$_{17}$H$_{11}$Cl$_2$NO$_2$ : C, 61.47; H, 3.34; N, 4.22; Found: C, 61.71; H, 3.36; N, 4.20. | 81% | 2,5-Dihydroxy-3-(2-cyclopropyl-1H-indol-3-yl)-[1,4]benzoquinone<br>mp 179–180° C. IR(KBr): 3358, 2921, 1632, 1461, 1364, 1187, 955, 741cm$^{-1}$. $^1$H NMR(d$_6$-acetone): δ 10.0(1H, br s), 9.2–10.0(2H, br), 7.27(1H, d, J=7.8Hz), 7.21(1H, d, J=7.8Hz), 7.01(1H, t, J=7.8Hz), 6.93(1H, t, J=7.8Hz), 6.05(1H, s), 1.99 (1H, m), 0.89(4H, m). $^{13}$C NMR(d$_6$-acetone): δ 140.5, 135.7, 128.6, 120.7, 119.4, 119.1, 111.9, 110.7, 103.5, 102.6, 9.2, 7.1. HRMS (FAB) Calculated for C$_{17}$H$_{13}$NO$_4$ [M$^+$]: 295.0845. Found: 295.0846. |
| 2,5-Dichloro-3-(2-phenyl-1H-indol-3-yl)-[1,4]benzoquinone<br>Blue crystals from benzene/hexane. mp 170–171° C. $^1$H NMR(CDCl$_3$): δ 7.20(1H, m), 7.21(1H, s), 7.28–7.31(2H, m), 7.36–7.43(5H, m), 7.47(1H, m), 8.61(1H, br s). $^{13}$C NMR(CDCl$_3$): δ 104.7, 111.9, 120.4, 121.3, 123.3, 127.3, 127.5, 129.1, 129.4, 132.4, 133.4, 136.2, 139.6, 140.5, 141.3, 144.7, 176.5, 177.8. IR(KBr): 3384, 3056, 1683, 1565, 1446, 1248cm$^{-1}$. Anal. Calcd. for C$_{20}$H$_{11}$Cl$_2$NO$_2$: C, 65.24; H, 3.01; N, 3.73. Found: C, 64.61; H, 3.14; N, 3.76. | 65% | 2,5-Dihydroxy-3-(2-phenyl-1H-indol-3-yl)-[1,4]benzoquinone<br>Green crystals from benzene/hexane. mp 227–228° C. $^1$H NMR(d$_6$-acetone): δ 10.8(1H, br s), 9.0–10.0 (2H, br), 7.67(2H, m), 7.45(1H, m), 7.38(3H, m), 7.29(1H, m), 7.12(1H, t, J=8.4Hz), 7.03(1H, t, J=7.2Hz), 6.06(1H, s). $^{13}$C NMR(d$_6$-acetone): δ 137.0, 136.7, 133.7, 129.1, 128.8, 127.7, 127.2, 122.1, 120.3, 119.6, 112.1, 111.4, 103.8, 102.3. IR (KBr): 3422, 3303, 3051, 1629, 1355, 1296cm$^{-1}$. HRMS (FAB) Calcd. For C$_{20}$H$_{13}$NO$_4$ [M$^+$]: 331.0845. Found: 331.0846. |
| 2,5-Dichloro-3-(1-methyl-1H-indol-3-yl)-[1,4]benzoquinone<br>Blue crystals from benzene/hexane. mp 156.1–156.2° C. IR (KBr): 3142, 3057, 2911, 1683, 1656, 1559, 749cm$^{-1}$. $^1$H NMR(CDCl$_3$): δ 3.91(3H, s), 7.21(1H, s), 7.23(1H, m), 7.31(1H, m), 7.39(1H, d, J=9.3Hz), 7.40(1H, dd, J=0.9, 6.9Hz). $^{13}$C NMR(CDCl$_3$): δ 33.9, 105.6, 110.3, 121.1, 122.3, 122.9, 126.0, 133.5, 134.4, 137.0, 138.4, 144.1, 178.0. Anal. Calcd. for C$_{15}$H$_9$Cl$_2$NO$_2$: C, 58.85; H, 2.97; N, 4.58. Found: C, 58.69; H, 3.07; N, 4.57. | 62% | 2,5-Dihydroxy-3-(1-methyl-1H-indol-3-yl)-[1,4]benzoquinone<br>Green crystals from benzene/hexane. mp 201–202° C. IR(KBr): 3286, 1627, 1533, 1355, 1298, 1234, 1188, 935, 735cm$^{-1}$. $^1$H NMR(d$_6$-acetone): δ 9.0–10.0 (2H, br)7.52(1H, d, J=8.1Hz), 7.49(1H, s), 7.41(1H, d, J=8.4Hz), 7.19(1H, t, J=7.5Hz), 7.05(1H, t, J=7.5Hz),, 6.01(1H, s), 3.89(3H, s). $^{13}$C NMR(d$_6$-acetone): δ 137.0, 131.6, 127.4, 122.2, 121.5, 119.2, 111.8, 109.5, 103.6, 103.2, 32.4. HRMS (FAB) Calculated for C$_{15}$H$_{11}$NO$_4$ [M$^+$]: 269.0688. Found: 269.0681. |
| 2,5-Dichloro-3-(2-ethyl-1H-indol-3-yl)-[1,4]benzoquinone<br>This compound was synthesized according to the general procedure A from 2-ethyl-1H-indole(100 mg, 0.689 mmol) and 2,5-dichloro-1,4-benzoquinone(244 mg, 1.38 mmol) and was obtained as a blue solid(209 mg, 95%). mp 143–144° C. $R_f$ =0.38(3:7, EtOAc/hexane). $^1$H NMR(CDCl$_3$): δ 8.48(bs, NH), 7.29(m, 1H), 7.20(s, 1H), 7.19–7.08(m, 3H), 2.61(qd, J=7.5, 3.0Hz, 2H), 1.27(t, J=7.5Hz, 3H); $^1$H NMR(d$_6$-acetone): δ 10.62(1H, br s), 7.40(1H, s), 7.38 (1H, d, J=8.1Hz), 7.24(1H, d, J=8.1Hz), 7.09(1H, t, J=8.1Hz), 8.1Hz), 7.01(1H, t, J=8.1Hz), 7.71(2H, q, J=7.8Hz), 1.30(3H, t, J=7.8). $^{13}$C NMR(CDCl$_3$): δ 177.7, 176.6, 144.3, 142.1, 140.2, 139.5, 135.2, 133.0, 126.4, 121.9, 120.5, 119.6, 110.9, 103.7, 21.2, 13.4. IR(KBr): 3394, 3050, 2973, 1677, 1646, 1563, 1447, 1241, 1038, 746cm$^{-1}$. Anal. Calcd. for C$_{16}$H$_{11}$Cl$_2$NO$_2$: C, 60.02; H, 3.46; Cl, 22.15; N, 4.37. Found. C, 59.99; H, 3.51; N, 4.18. | 77% | 2,5-Dihydroxy-3-(2-ethyl-1H-indol-3-yl)-[1,4]benzoquinone<br>Green crystals from benzene/hexane. mp 157–158° C. IR(KBr): 3395, 3320, 3062, 2976, 1629, 1361, 1291, 1173cm$^{-1}$. $^1$H NMR(d$_6$-acetone): δ 10.27(1H, br s), 9.0–10.0(2H, br), 7.31(1H, d, J=7.8Hz), 7.22 (1H, d, J=7.8Hz), 6.94–7.08(2H, m), 6.04(1H, s), 2.68(2H, q, J=7.8Hz), 1.28(3H, t, J=6.9Hz). $^{13}$C NMR(d$_6$-acetone): δ 140.8, 136.2, 128.4, 120.7, 119.8, 119.0, 111.8, 110.7, 103.5, 101.1, 20.9, 13.4. HRMS (FAB) Calcd. For C$_{16}$H$_{13}$NO$_4$ [M$^+$]: 283.0845. Found: 283.0846. |
| 2,5-Dichloro-3-(2-isopropyl-1H-indol-3-yl)-[1,4]benzoquinone<br>This compound was synthesized according to the general procedure A from 2-isoprenyl-1H-indole(50 mg, 0.314 mmol) and 2,5-dichloro-1,4-benzoquinone(111 mg, 0.629 mmol) and was obtained as a blue solid(74 mg, 70%). mp 187–188° C. $R_f$ =0.26(1:4, EtOAc/hexane). $^1$H NMR (CDCl$_3$)δ 8.40(bs, NH), 7.36(m, 1H), 7.22(s, 1H), 7.21–7.08(m, 3H). 2.88(septet, J=6.9Hz, 1H), 1.35(d, J=6.9Hz, 3H), 1.27(d, J=6.9Hz, 3H). $^{13}$C NMR(CDCl$_3$)δ 177.7, 176.6, 145.8, 144.4, 140.9, 139.7, 135.1, 133.1, 126.1, 122.0, 120.4, 119.5, 111.0, 102.6, 27.4, 22.9, 22.3. IR (KBr): 3421, 3312, 3053, 2963, 1671, 1569, 1440, 1241, 1031, 759cm$^{-1}$. HRMS (EI) Calcd. For C$_{17}$H$_{13}$Cl$_2$NO$_2$ [M$^+$]: 333.0323. Found: 333.0313 | 80% | 2,5-Dihydroxy-3-(2-isopropyl-1H-indol-3-yl)-[1,4]benzoquinone<br>mp 140° C.(dec). IR(KBr): 3352, 3290, 2926, 1627, 1363, 1306, 1189, 955, 744cm$^{-1}$. $^1$H NMR(d$_6$-acetone): δ 10.29(1H, br s), 9.0–10.0(2H, br), 7.31 (1H, d, J=7.8Hz), 7.21(1H, d, J=7.8Hz), 7.02(1H, t, J=7.8Hz), 6.93(1H, t, J=7.8Hz), 6.05(1H, s), 3.03(1H, m), 1.32(6H, d, J=6.9Hz). $^{13}$C NMR(d$_6$-acetone): δ 144.7, 136.3, 128.3, 120.7, 119.7, 118.9, 111.9, 110.8, 103.5, 100.1, 27.3, 22.2. HRMS (FAB) Calculated for C$_{17}$H$_{15}$NO$_4$ [M$^+$]: 297.1001. Found: 297.0997. |

TABLE 2-continued

| Starting Product | Yield | End Product |
|---|---|---|
| 2,5-Dichloro-3-(2-tert-butyl-1H-indol-3-yl)-[1,4]benzoquinone<br>mp 235–236° C. IR(KBr)3419, 3317, 3059, 2965, 1673, 1585, 1462, 1245, 1029, 742cm$^{-1}$. $^1$H NMR(d6-acetone): δ 10.40(1H, br s), 7.47(1H, s), 7.35(1H, d, J=7.8Hz), 7.23(1H, d, J=7.8Hz), 7.08(1H, t, J=7.8Hz), 6.95(1H, t, J=7.8Hz), 1.38(9H, s). $^{13}$C NMR(CDCl$_3$): δ 178.0, 177.7, 145.3, 145.1, 143.2, 142.7, 134.9, 133.5, 127.1, 122.6, 120.6, 118.3, 111.1, 102.1, 33.6, 30.5. HRMS (EI) Calcd. For C$_{18}$H$_{15}$Cl$_2$NO$_2$ [M$^+$]: 347.0480. Found: 347.0491. | 52% | 2,5-Dihydroxy-3-(2-tert-butyl-1H-indol-3-yl)-[1,4]benzoquinone<br>mp 195° C.(dec). IR(KBr): 3434, 3329, 2963, 1634, 1597, 1365, 1239, 944, 745cm$^{-1}$. $^1$H NMR(d6-acetone): δ 10.13(1H, br s), 8.8–9.8(2H, br), 7.27 (1H, d, J=6.0Hz), 7.14(1H, d, J=6.0Hz), 6.99(1H, t, J=6.0Hz), 6.88(1H, t, J=6.0Hz), 6.05(1H, s), 1.34(9H, s). $^{13}$C NMR(d$_6$-acetone): δ 145.2, 135.6, 129.3, 121.0, 118.9, 118.5, 113.8, 110.7, 103.8, 99.5, 33.3, 29.7. HRMS (FAB) Calculated for C$_{17}$H$_{13}$NO$_4$ [M$^+$]: 311.1158. Found: 311.1158 |
| 2,5-Dichloro-3-[2-(1-methyl-cyclopropyl)-1H-indol-3-yl]-[1,4]benzoquinone<br>Blue needles from benzene/hexane. mp 170–171° C. $^1$H NMR(d$_6$-acetone): 0.53–0.60(1H, m), 0.64–0.70(1H, m), 0.70–0.77(1H, m), 0.92–0.98(1H, m), 1.48(3H, s), 7.01 (1H, dt, J=1.2, 7.5Hz), 7.10(1H, dt, J=1.2, 7.5Hz), 7.24 (1H, dd, J=0.6, 7.2Hz), 7.37(1H, d, J=7.8Hz), 7.39(1H, s), 10.70(1H, s). $^{13}$C NMR(d$_6$-acetone): 13.3, 14.1, 15.1, 24.5, 103.6, 111.4, 119.7, 119.9, 121.9, 126.8, 133.8, 136.0, 140.4, 140.8, 143.9, 144.0, 177.1, 177.9. IR(KBr): 3409, 3059, 3004, 2966, 2927, 1662, 1620, 1567, 1435, 1270, 1241, 1028, 755cm$^{-1}$. Anal. Calcd. for C$_{18}$H$_{13}$Cl$_2$NO$_2$: C, 62.45; H, 3.78; N, 4.05. Found: C, 62.30; H, 3.77; N, 3.94. | 87% | 2,5-Dihydroxy-3-[2-(1-methyl-cyclopropyl)-1H-indol-3-yl]-[1,4]benzoquinone<br>The solution was concentrated and purified by flash column chromatography(oxalic acid-coated silica gel)using 30% EtOAc in hexane as the eluent to afford 2,5-dihydroxy-3-[2-(1-methyl-cyclopropyl)-1H-indol-3-yl]-[1,4]benzoquinone(0.044 g, 87%)as dark blue needles from acetone/hexane. mp 103° C. (dec). $^1$H NMR(d$_6$-acetone): 0.55–0.62(2H, m), 0.81–0.87(2H, m), 1.45(3H, s), 6.08(1H, s), 6.93 (1H, dt, J=0.9, 8.1Hz), 7.04(1H, dt, J=1.2, 8.1Hz), 7.22(1H, d, J=7.8Hz), 7.31(1H, dd, J=0.9, 8.1Hz), 9.0–10.1(2H, br s), 10.34(1H, br s). $^{13}$C NMR(d$_6$-acetone): 13.3, 14.8, 24.4, 101.4, 103.6, 110.8, 112.3, 119.0, 119.5, 121.1, 128.4, 135.8, 142.2. IR(KBr): 3300, 3077, 2958, 2924, 1640, 1360, 1190, 746cm$^{-1}$. HRMS (EI): calculated for C$_{18}$H$_{15}$NO$_4$ 309.1001; found 309.0999. |
| 2,5-Dichloro-3-[2-(1-methyl-cyclohexyl)-1H-indol-3-yl]-[1,4]benzoquinone<br>Blue needles from benzene/hexane. mp 184–185° C. $^1$H NMR(d$_6$-acetone): 1.36(3H, s), 1.38–1.66(10H, m), 6.96 (1H, dt, J=1.2, 7.2Hz), 7.08(1H, dt, J=1.2, 7.2Hz), 7.23 (1H, d, J=7.8Hz), 7.37(1H, d, J=8.1Hz), 7.45(1H, s), 10.39(1H, br s). $^{13}$C NMR(d$_6$-acetone): 22.6, 22.8, 26.2, 27.4, 37.5, 37.8, 38.2, 102.4, 111.2, 118.5, 119.5, 121.5, 127.4, 134.0, 135.6, 142.4, 142.8, 143.9, 145.0, 177.8. IR (KBr): 3421, 3320, 3054, 2936, 2863, 1672, 1618, 1573, 1515, 1457, 1205, 1024cm$^{-1}$. Anal. Calcd. for C$_{21}$H$_{19}$Cl$_2$NO$_2$: C, 64.96; H, 4.93; N, 3.61. Found: C, 65.04; H, 4.89; N, 3.63. | 90% | 2,5-Dihydroxy-3-[2-(1-methyl-cyclohexyl)-1H-indol-3-yl]-[1,4]benzoquinone<br>Dark blue needles from acetone/hexane. mp 191–192° C. $^1$H NMR(d$_6$-acetone): 1.34(3H, s), 1.25–1.60 (10H, m), 6.08(1H, s), 6.90(1H, dt, J=1.2, 6.9Hz), 7.02(1H, dt, J=1.2, 7.8Hz), 7.17(1H, d, J=7.8Hz), 7.32(1H, dt, J=0.9, 8.1Hz), 8.5–10.0(2H, br s), 10.12(1H, br s). $^{13}$C NMR(d$_6$-acetone): 23.0, 26.3, 37.6, 37.8, 100.4, 103.8, 110.7, 113.8, 118.5, 118.8, 120.9, 129.4, 135.6, 143.8. IR(KBr): 3270, 2975, 2932, 2862, 1700, 1535, 1465, 938, 717cm$^{-1}$. HRMS (EI): calcd. for C$_{21}$H$_{21}$NO$_4$ 351.1471, found 351.1471. |
| 3-(4-Fluoro-1H-indol-3-yl)-2,5-dichloro-[1,4]benzoquinone<br>Blue needles from benzene/hexane. mp 161–162° C. $^1$H NMR(d$_6$-acetone): 6.79(1H, ddd, J=0.7, 7.6, 11.2Hz), 7.15(1H, dt, J=5.2, 7.6Hz), 7.34(1H, d, J=8Hz), 7.38 (1H, s), 7.66(1H, d, J=2.8Hz), 11.15(1H, s). $^{13}$C NMR (d$_6$-acetone): 104.5, 105.7, 105.9, 108.6, 123.1, 123.2, 129.2, 133.6, 139.1, 143.6, 154.9, 157.2, 177.5 177.8. IR (KBr): 3386, 3067, 1671, 1577, 1505, 1422, 1318, 1265, 1226, 1019cm$^{-1}$. Anal. Calcd. for C$_{14}$H$_6$Cl$_2$FNO$_2$: C, 54.22; H, 1.95; N, 4.52. Found: C, 54.15; H, 1.89; N, 4.58. | 65% | 3-(4-Fluoro-1H-indol-3-yl)-2,5-dihydroxy-[1,4]benzoquinone<br>Dark blue needles from acetone/hexane. mp 248° C. (dec). $^1$H NMR(d$_6$-acetone): 6.04(1H, s), 6.70(1H, dd, J=7.8, 11.1Hz), 7.09(1H, dt, J=5.1, 8.1Hz), 7.28(1H, dd, J=3.3, 8.1Hz), 7.43(1H, d, J=2.4Hz), 8.0–10.4(2H, br s), 10.76(1H, br s). $^{13}$C NMR (d$_6$-acetone): 103.5, 104.6, 104.9, 108.0, 122.2, 122.3, 126.8, 139.4, 155.0, 158.3. IR(KBr): 3452, 2954, 2852, 1661, 1639, 1359, 1232, 1192, 1035, 934cm$^{-1}$. HRMS (EI): calcd. for C$_{14}$H$_8$FNO$_4$ 273.0437, found 273.0436. |
| 3-(4-Chloro-1H-indol-3-yl)-2,5-dichloro-[1,4]benzoquinone<br>Blue needles from benzene/hexane. mp 204–205° C. $^1$H NMR(d$_6$-acetone): 7.07(1H, dd, J=0.8, 7.6Hz), 7.15(1H, t, J=7.6Hz), 7.40(1H, s), 7.49(1H, dd, J=0.8, 8.0Hz), 7.60(1H, d, J=2.8Hz), 11.17(1H, br s). $^{13}$C NMR(d$_6$-acetone): 106.3, 111.4, 121.0, 123.2, 124.4, 125.0, 128.4, 133.6, 137.9, 140.5, 140.9, 143.9, 177.7, 177.9. IR(KBr): 3350, 3115, 3068, 1673, 1659, 1572, 1416, 1274, 1196, 1023cm$^{-1}$. Anal. Calcd. for C$_{14}$H$_6$Cl$_3$NO$_2$: C, 51.49; H, 1.85. Found: C, 51.33; H, 2.00. | 74% | 3-(4-Chloro-1H-indol-3-yl)-2,5-dihydroxy-[1,4]benzoquinone<br>Dark blue needles from acetone/hexane. mp 230° C. (dec). $^1$H NMR(d$_6$-acetone): 6.05(1H, s), 7.01(1H, dd, J=0.8, 7.6Hz), 7.10(1H, t, J=8.0Hz), 7.40 (1H, d, J=2.4Hz), 7.44(1H, dd, J=0.8, 8.0Hz), 8.6–10.1(2H, br s), 10.77(1H, br s)$^{13}$C NMR(d$_6$-acetone): 103.6, 104.0, 110.9, 112.5, 120.4, 122.3, 124.9, 125.6, 127.2, 138.1. IR(KBr): 3324, 2953, 1628, 1536, 1484, 1424, 1353, 1187, 927cm$^{-1}$. HRMS (FAB) : calcd. for C$_{14}$H$_8$ClNO$_4$ 289.0142, found 289.0143. |

TABLE 2-continued

| Starting Product | Yield | End Product |
|---|---|---|
| 3-(4-Bromo-1H-indol-3-yl)-2,5-dichloro-[1,4]benzoquinone<br>Blue needles from benzene/hexane. mp 247–248° C. $^1$H NMR(d$_6$-acetone): 7.09(1H, t, J=8.0Hz), 7.25(1H, dd, J=0.8, 8.0Hz), 7.41(1H, s), 7.54(1H, dd, J=0.8, 8.0Hz), 7.60(1H, d, J=3.2Hz), 11.11(1H, br s). $^{13}$C NMR(d$_6$-acetone): 107.3, 111.2, 111.9, 113.1, 123.5, 124.3, 126.0, 128.2, 133.6, 137.7, 141.0, 144.1, 177.6, 177.9. IR(KBr): 3367, 3116, 3068, 1651, 1613, 1570, 1517, 1480, 1412, 1021, 875cm$^{-1}$. Anal. Calcd. for C$_{14}$H$_6$BrCl$_2$NO$_2$: C, 45.32; H, 1.63. Found: C, 45.38; H, 1.84. | 86% | 3-(4-Bromo-1H-indol-3-yl)-2,5-dihydroxy-[1,4]benzoquinone<br>Dark blue needles from acetone/hexane. mp 232° C. (dec). $^1$H NMR(d$_6$-acetone): 6.06(1H, s), 7.04(1H, t, J=8.0Hz), 7.20(1H, dd, J=0.8, 8.0Hz), 7.41 (1H, d, J=2.8Hz), 7.50(1H, dd, J=0.8, 8.0Hz), 9.0–10.0(2H, br s), 10.77(1H, br s). $^{13}$C NMR(d$_6$-acetone): 103.6, 104.9, 111.4, 113.7, 122.7, 123.7, 126.3, 127.2, 127.3, 137.8. IR(KBr). 3326, 2983, 2854, 1629, 1540, 1341, 1187, 934cm$^{-1}$. HRMS (EI): calcd. for C$_{14}$H$_8$BrNO$_4$ 332.9637, found 332.9634. |
| 2,5-Dichloro-3-(4-methoxy-1H-indol-3-yl)-[1,4]benzoquinone<br>Blue needles from benzene/hexane. mp 195–196° C. $^1$H NMR(d$_6$-acetone): 3.76(1H, s), 6.58(1H, dd, J=3.6, 5.1Hz), 7.11(1H, s), 7.12(1H, d, J=1.5Hz), 7.35(1H, s), 7.56 (1H, d, J=3Hz), 10.86(1H, br s). $^{13}$C NMR(d$_6$-acetone): 55.0, 101.2, 105.4, 106.5, 123.6, 126.8, 127.0, 133.2, 136.4, 138.0, 141.9, 143.6, 153.3, 177.6, 177.8. IR(KBr): 3324, 3042, 2967, 1676, 1638, 1546, 1486, 1260, 1229, 1009cm$^{-1}$. Anal. Calcd. for C$_{15}$H$_9$Cl$_2$NO$_3$: C, 55.93; H, 2.82; N, 4.35. Found: C, 56.09; H, 2.87; N, 4.32. | 82% | 2,5-Dihydroxy-3-(4-methoxy-1H-indol-3-yl)-[1,4]benzoquinone<br>Dark green needles from acetone/hexane. mp 225° C. (dec). $^1$H NMR(d$_6$-acetone): 3.71(3H, s), 6.00(1H, s), 6.48(1H, dd, J=3.2, 5.6Hz), 7.03(1H, d, J=2.0Hz), 7.04(1H, s), 7.23(1H, d, J=2.8Hz), 8.5–9.8 (2H, br s), 10.42(1H, br s). $^{13}$C NMR(d$_6$-acetone): 54.9, 100.2, 103.2, 103.7, 105.0, 113.9, 118.2, 122.6, 124.6, 138.2, 154.3. IR(KBr): 3314, 2958, 2933, 1634, 1511, 1357, 1200, 1089, 936cm$^{-1}$. HRMS (EI): calcd. for C$_{15}$H$_{11}$NO$_5$ 285.0637, found 285.0635. |
| 3-(4-Benzyloxy-1H-indol-3-yl)-2,5-dichloro-[1,4]benzoquinone<br>Blue needles from benzene/hexane. mp 193–194° C. $^1$H NMR(d$_6$-acetone): 5.01(2H, s), 6.64(1H, dd, J=2.4, 6.4Hz), 7.06(1H, s), 7.4–7.7(2H, m), 7.23–7.34(5H, m), 7.45 (1H, d, J=2.8Hz), 10.79(1H, br s). $^{13}$C NMR(d$_6$-acetone): 70.3, 102.1, 105.6, 106.3, 117.8, 123.5, 126.3, 127.8, 128.0, 128.6, 132.9, 137.5, 138.1, 141.7, 143.8, 152.7, 177.2, 177.8. IR(KBr): 3346, 3116, 3063, 3034, 1673, 1656, 1572, 1508, 1453, 1423, 1270cm$^{-1}$. Anal. Calcd. for C$_{21}$H$_{13}$Cl$_2$NO$_3$: C, 63.34; H, 3.29. Found: C, 63.26; H, 3.40. | 81% | 3-(4-Benzyloxy-1H-indol-3-yl)-2,5-dihydroxy-[1,4]benzoquinone<br>Dark green needles from acetone/hexane. mp 188–189° C. $^1$H NMR(d$_6$-acetone): 5.03(2H, s), 5.88 (1H, s), 6.60(1H, dd, J=1.6, 7.2Hz), 7.06(1H, q, J=8.4Hz), 7.07(1H, d, J=2.8Hz), 7.21(1H, d, J=2.4Hz), 7.24–7.32(3H, m), 7.34(1H, d, J=1.6Hz), 7.36(1H, d, J=2.0Hz), 8.8–9.8(2H, br s), 10.44 (1H, br s). $^{13}$C NMR(d$_6$-acetone): 69.7, 101.1, 103.0, 103.7, 105.2, 113.8, 118.3, 122.6, 124.5, 127.2, 127.6, 128.4, 137.9, 138.3, 153.4. IR(KBr): 3396, 3308, 2918, 2869, 1628, 1506, 1443, 1318, 1075cm$^{-1}$. HRMS (EI): calcd. for C$_{21}$H$_{15}$NO$_5$ 361.0950, found 361.0952. |
| 2,5-Dichloro-3-(4-methyl-1H-indol-3-yl)-[1,4]benzoquinone<br>Blue needles from benzene/hexane. mp 192–193° C. $^1$H NMR(d$_6$-acetone): 2.28(3H, s), 6.83(1H, dt, J=0.6, 5.4Hz), 7.06(1H, t, J=5.7Hz), 7.32(1H, d, J=6Hz), 7.39 (1H, s), 7.44(1H, d, J=2.1Hz), 10.77(1H, br s). $^{13}$C NMR (d$_6$-acetone): 19.3, 107.1, 110.0, 122.0, 122.5, 126.1, 127.1, 129.8, 133.8, 136.9, 140.4, 142.0, 143.7, 177.9, 178.3. IR (KBr): 3369, 3114, 3068, 1669, 1553, 1511, 1267, 1182, 1019, 876, 753cm$^{-1}$. Anal. Calcd. for C$_{15}$H$_9$Cl$_2$NO$_2$: C, 58.85; H, 2.96. Found: C, 58.85; H, 2.91. | 81% | 2,5-dihydroxy-3-(4-methyl-1H-indol-3-yl)-[1,4]benzoquinone<br>Dark green needles from acetone/hexane. mp 220° C. (dec). $^1$H NMR(d$_6$-acetone): 2.36(3H, s), 6.05(1H, s), 6.76(1H, dt, J=0.9, 6.9Hz), 7.00(1H, t, J=7.6Hz), 7.23(1H, d, J=2.4Hz), 7.27(1H, d, J=8.1Hz), 8.5–10.2(2H, br s), 10.41(1H, br s). $^{13}$C NMR (d$_6$-acetone): 18.7, 103.7, 104.4, 109.6, 114.1, 121.0, 121.7, 125.6, 126.8, 130.1, 136.9. IR(KBr): 3417, 3328, 3128, 2959, 2927, 2861, 1628, 1533, 1357, 934cm$^{-1}$. HRMS (EI): calcd. for C$_{15}$H$_{11}$NO$_4$ 269.0688, found 269.0688. |
| 3-(5-Fluoro-1H-indol-3-yl)-2,5-dichloro-[1,4]benzoquinone<br>Blue needles from benzene/hexane. mp 175–176° C. $^1$H NMR(d$_6$-acetone): 7.00(1H, dt, J=2.1, 9.0Hz), 7.16(1H, dd, J=1.2, 10.2Hz), 7.35(1H, s), 7.53(1H, dd, J=4.5, 8.7Hz), 7.79(1H, d, J=2.7Hz), 11.1(1H, br s). $^{13}$C NMR(d$_6$-acetone): 106.4, 106.7, 110.3, 110.7, 113.2, 113.3, 132.2, 133.0, 133.3, 143.8, 156.5, 159.6, 177.4, 177.8. IR(KBr): 3394, 3131, 3063, 2956, 2925, 1678, 1656, 1570, 1423, 1258, 1011cm$^{-1}$. Anal. Calcd. for C$_{14}$H$_6$Cl$_2$FNO$_2$: C, 54.22; H, 1.95; N, 4.52. Found: C, 54.30; H, 2.01; N, 4.54. | 72% | 3-(5-Fluoro-1H-indol-3-yl)-2,5-dihydroxy-[1,4]benzoquinone<br>Dark blue needles from acetone/hexane. mp 225–226° C. $^1$H NMR(d$_6$-acetone): 6.03(1H, s), 6.93(1H, dt, J=2.4, 9.2Hz), 7.26(1H, dd, J=2.4, 6.4Hz), 7.44 (1H, dd, J=4.8, 8.8Hz), 7.69(1H, d, J=2.4Hz), 8.2–10.4(2H, br s), 10.69(1H, br s). $^{13}$C NMR(d$_6$-acetone): 103.2, 106.6, 106.9, 109.5, 109.8, 112.3, 112.4, 129.6, 133.0, 156.5, 158.8. IR(KBr): 3449, 3294, 2956, 2855, 1627, 1486, 1335, 1230, 1184, 933cm$^{-1}$. HRMS (EI): calcd. for C$_{14}$H$_8$FNO$_4$ 273.0437, found 273.0442. |
| 3-(5-Chloro-1H-indol-3-yl)-2,5-dichloro-[1,4]benzoquinone<br>Blue needles from benzene/hexane. mp 189–190° C. $^1$H NMR(CDCl$_3$): 7.24(1H, s), 7.25(1H, dd, J=0.9, 2.1Hz), 7.36(1H, d, J=0.9Hz), 7.37–7.39(1H, m), 7.58(1H, d, J=3Hz), 8.60(1H, s). $^{13}$C NMR(d$_6$-acetone): 106.4, 113.6, 120.9, 122.4, 125.7, 127.2, 131.7, 133.4, 134.9, 137.5, 138.7, 143.9, 177.5, 177.9. IR(KBr): 3331, 3053, 1675, 1652, 1568, 1505, 1460, 1274, 1247, 803cm$^{-1}$. Anal. Calcd. for C$_{14}$H$_6$Cl$_3$NO$_2$: C, 51.49; H, 1.85; N, 4.29. Found: C, 51.51; H, 2.01; N, 4.26. | 62% | 3-(5-Chloro-1H-indol-3-yl)-2,5-dihydroxy-[1,4]benzoquinone<br>Dark blue needles from acetone/hexane. mp 192–193° C. $^1$H NMR(d$_6$-acetone): 6.03(1H, s), 7.12(1H, dd, J=2.1, 8.7Hz), 7.46(1H, dd, J=1.8, 8.7Hz), 7.56(1H, d, J=1.8Hz), 7.67(1H, d, J=2.7Hz), 8.5–10.0(2H, br s), 10.78(1H, br s). $^{13}$C NMR(d$_6$-acetone): 103.2, 104.6, 111.3, 112.9, 121.3, 121.6, 124.6, 128.0, 129.3, 134.8. IR(KBr): 3409, 3302, 2917, 2879, 1631, 1529, 1354, 1231, 933cm$^{-1}$. HRMS (EI): calcd. for C$_{14}$H$_8$ClNO$_4$ 289.0142, found 289.0144. |

TABLE 2-continued

| Starting Product | Yield | End Product |
|---|---|---|
| 3-(5-Bromo-1H-indol-3-yl)-2,5-dichloro-[1,4]benzoquinone<br>Blue needles from benzene/hexane. mp 205–206° C. $^1$H NMR($d_6$-acetone): 7.31(1H, dd, J=2.0, 8.8Hz), 7.37(1H, s), 7.50(1H, d, J=8.4Hz), 7.62(1H, s), 7.76(1H, d, J=2.8Hz), 11.14(1H, s). $^{13}$C NMR($d_6$-acetone): 106.3, 113.3, 114.0, 123.9, 125.0, 127.8, 131.5, 133.4, 135.2, 137.5, 138.8, 143.9, 177.5, 177.9. IR(KBr): 3382, 3138, 3058, 1671, 1650, 1571, 1457, 1271, 1245, 1113, 1010cm$^{-1}$. Anal. Calcd. for $C_{14}H_6BrCl_2NO_2$: C, 45.32; H, 1.63; N, 3.78. Found: C, 45.56; H, 1.77; N, 3.70. | 56% | 3-(5-Bromo-1H-indol-3-yl)-2,5-dihydroxy-[1,4]benzoquinone<br>Dark blue needles from acetone/hexane. mp 210–211° C. $^1$H NMR($d_6$-acetone): 6.02(1H, s), 7.24(1H, dd, J=1.8, 8.7Hz), 7.42(1H, d, J=8.7Hz), 7.65(1H, d, J=2.7Hz), 7.71(1H, d, J=2.1Hz), 8.5–10.2(2H, br s), 10.82(1H, br s). $^{13}$C NMR($d_6$-acetone): 103.2, 104.5, 112.2, 113.3, 124.2, 124.4, 128.6, 129.0, 129.1, 135.1 IR(KBr): 3309, 3035, 1631, 1455, 1349, 1322, 1230, 930cm$^{-1}$. HRMS (EI): calcd. for $C_{14}H_8BrNO_4$ 332.9637, found 332.9636. |
| 2,5-Dichloro-3-(5-hydroxy-1H-indol-3-yl)-[1,4]benzoquinone<br>Blue needles from benzene/hexane. mp 101(dec)° C. $^1$H NMR($d_6$-acetone): 6.80(2H, m), 7.33(1H, s), 7.34(1H, m), 7.65(1H, d, J=3.3Hz), 7.92(1H, br s), 10.86(1H, br s). $^{13}$C NMR($d_6$-acetone): 103.7, 105.9, 106.2, 112.4, 112.6, 113.4, 113.8, 131.1, 131.1, 131.3, 133.4. IR(KBr): 3500, 3121, 1698, 1566, 1167, 1102, 851, 694, 617cm$^{-1}$. Anal. Calcd. for $C_{14}H_7Cl_2NO_3$: C, 54.57; H, 2.29. Found: C, 54.95; H, 2.62. | 70% | 2,5-Dihydroxy-3-(5-hydroxy-1H-indol-3-yl)-[1,4]benzoquinone<br>Dark green needles from acetone/hexane. mp 235° C. (dec). $^1$H NMR($d_6$-acetone): 6.00(1H, s), 6.73(1H, dd, J=2.4, 8.7Hz), 6.92(1H, d, J=2.4Hz), 7.26 (1H, d, J=8.7Hz), 7.51(1H, d, J=3.0Hz), 7.6–7.8 (1H, br s), 8.0–10.0(2H, br s), 10.39(1H, br s). $^{13}$C NMR($d_6$-acetone): 103.1, 104.0, 106.2, 111.7, 112.2, 127.8, 128.0, 128.2, 131.1, 151.0 IR(KBr): 3302, 1697, 1630, 1463, 1357, 1202, 935, 856, 802cm$^{-1}$. HRMS (EI): calcd. for $C_{14}H_9NO_5$ 271.0481, found 271.0482. |
| 2,5-Dichloro-3-(5-methoxy-1H-indol-3-yl)-[1,4]benzoquinone<br>Blue needles from benzene/hexane. mp 195–196° C. $^1$H NMR(CDCl$_3$): 6.78(1H, d, J=2.4Hz), 6.93(1H, dd, J=2.1, 8.4Hz), 7.23(1H, s), 7.34(1H, d, J=9.0Hz), 7.54 (1H, d, J=3.0Hz), 8.62(1H, br s). $^{13}$C NMR($d_6$-acetone): 55.2, 103.8, 106.7, 112.4, 112.8, 126.5, 130.9, 131.0, 131.4, 133.4, 139.8, 143.7, 154.8, 177.8, 178.0. IR(KBr): 3328, 3043, 2924, 2855, 1675, 1638, 1543, 1484, 1260, 1227cm$^{-1}$. Anal. Calcd. for $C_{15}H_9Cl_2NO_3$: C, 55.93; H, 2.82; N, 4.35. Found: C, 55.72; H, 2.99; N, 4.24. | 63% | 2,5-Dihydroxy-3-(5-methoxy-1H-indol-3-yl)-[1,4]benzoquinone<br>Dark green needles from acetone/hexane. mp 178° C. (dec). $^1$H NMR($d_6$-acetone): 6.01(1H, s), 6.79(1H, dd, J=2.4, 8.7Hz), 7.06(1H, d, J=2.4Hz), 7.33 (1H, d, J=8.7Hz), 7.56(1H, d, J=3.0Hz), 8.5–10.0 (2H, br s), 10.47(1H, br s). $^{13}$C NMR($d_6$-acetone): 55.1, 103.1, 104.0, 104.5, 111.8, 112.0, 127.4, 128.2, 131.5, 154.1. IR(KBr): 3324, 3124, 3070, 3004, 2959, 2924, 2838, 1629, 1481, 1354, 1208cm$^{-1}$. HRMS (EI): calcd. for $C_{15}H_{11}NO_5$ 285.0637, found 285.0639. |
| 3-(5-Benzyloxy-1H-indol-3-yl)-2,5-dichloro-[1,4]benzoquinone<br>Blue needles from benzene/hexane. mp 164–165° C.. $^1$H NMR(CDCl$_3$). 5.08(2H, s, J=2.1Hz), 6.89(1H, s), 7.01 1H, dd, J=2.4, 8.7Hz), 7.22(1H, s), 7.26(1H, s), 7.30–7.50 (6H, m)7.53(1H, d, J=2.7Hz), 8.64(1H, br s). $^{13}$C NMR ($d_6$-acetone): 70.5, 105.6, 106.6, 112.8, 113.0, 126.3, 126.6, 127.8, 128.5, 131.0, 131.2, 131.7, 133.4, 138.1, 139.2, 143.8, 153.9, 177.7, 178.0. IR(KBr): 3342, 3065, 3037, 2907, 2874, 1674, 1564, 1480, 1426, 1258, 1009cm$^{-1}$. Anal. Calcd. for $C_{21}H_{13}Cl_2NO_3$: C, 63.34; H, 3.29; N, 3.52. Found: C, 63.24; H, 3.42; N, 3.49. | 63% | 3-(5-Benzyloxy-1H-indol-3-yl)-2,5-dihydroxy-[1,4]benzoquinone<br>Dark green needles from acetone/hexane. mp 198° C. (dec). $^1$H NMR($d_6$-acetone): 5.08(2H, s), 6.01(1H, s), 6.88(1H, dd, J=2.7, 8.7Hz), 7.20(1H, d, J=2.4Hz), 7.37(1H, d, J=1.8Hz), 7.3–7.4(3H, m), 7.48 (2H, d, J=6.6Hz), 7.58(1H, d, J=2.7Hz), 8.0–10.2 (2H, br s), 10.50(1H, br s). $^{13}$C NMR($d_6$-acetone): 70.5, 103.1, 104.6, 105.8, 112.0, 112.4, 127.4, 127.7, 127.8, 128.4, 128.5, 131.7, 138.5, 158.3. IR(KBr): 3110, 3035, 2919, 2866, 1632, 1479, 1358, 1195, 1018, 930cm$^{-1}$. HRMS (EI): calcd. for $C_{21}H_{15}NO_5$ 361.0950, found 361.0951. |
| 2,5-Dichloro-3-(5-methyl-1H-indol-3-yl)-[1,4]benzoquinone<br>Blue needles from benzene/hexane. mp 176–177° C.. $^1$H NMR($d_6$-acetone): 2.40(3H, s), 7.02(1H, dd, J=1.8, 8.4Hz), 7.20(1H, m), 7.33(1H, s), 7.40(1H, d, J=8.4Hz), 7.66(1H, dd, J=3.0Hz), 10.89(1H, br s). $^{13}$C NMR($d_6$-acetone): 21.27, 106.4, 111.9, 121.4, 123.9, 126.2, 129.3, 130.6, 133.4, 134.8, 136.4, 139.3, 143.6, 177.8, 177.9. IR (KBr): 3367, 3069, 2919, 2859, 1657, 1654, 1561, 1507, 1423, 1248, 1111cm$^{-1}$. Anal. Calcd. for $C_{15}H_9Cl_2NO_2$: C, 58.85; H, 2.96. Found: C, 58.95; H, 3.14. | 80% | 2,5-Dihydroxy-3-(5-methyl-1H-indol-3-yl)-[1,4]benzoquinone<br>Dark green needles from acetone/hexane. mp 190° C. (dec). $^1$H NMR($d_6$-acetone): 2.09(3H, s), 6.02(1H, s), 6.96(1H, dd, J=1.6, 8.4Hz), 7.31(1H, s), 7.32 (1H, d, J=8.4Hz), 7.53(1H, d, J=2.8Hz), 8.2–10.2 (2H, br s), 10.46(1H, br s). $^{13}$C NMR($d_6$-acetone): 21.1, 103.1, 104.2, 111.2, 112.2, 121.6, 123.1, 127.2, 127.7, 128.0, 134.8. IR(KBr): 3305, 3045, 1631, 1350, 1232, 1203, 932, 798cm$^{-1}$. HRMS (EI): calcd. for $C_{15}H_{11}NO_4$ 269.0688, found 269.0683. |
| 3-(6-Fluoro-1H-indol-3-yl)-2,5-dichloro-[1,4]benzoquinone<br>Blue needles from benzene/hexane. mp 168–169° C.. $^1$H NMR($d_6$-acetone): 6.95(1H, tt, J=1.8, 9Hz), 7.28(1H, dt, J=1.8, 9.6Hz), 7.37(1H, d, J=2.1Hz), 7.40(1H, d, J=5.4, 8.7Hz), 7.72(1H, d, J=2.4Hz), 11.12(1H, br s). $^{13}$C NMR($d_6$-acetone): 98.1, 98.4, 106.8, 108.6, 108.9, 122.6, 122.7, 131.0, 133.4, 143.8, 158.2, 161.4, 177.4, 177.9. IR (KBr): 3380, 3079, 2920, 1650, 1559, 1453, 1409, 1235, 1140, 1010, 882cm$^{-1}$. Anal. Calcd. for $C_{14}H_6Cl_2FNO_2$: C, 54.22; H, 1.95. Found: C, 54.48; H, 2.06. | 80% | 3-(6-Fluoro-1H-indol-3-yl)-2,5-dihydroxy-[1,4]benzoquinone<br>Dark green needles from acetone/hexane. mp 130–131° C.. $^1$H NMR($d_6$-acetone): 6.03(1H, s), 6.85 (1H, dt, J=2.4, 9.6Hz), 7.19(1H, dd, J=2.4, 9.9Hz), 7.51(1H, dd, J=5.4, 9.0Hz), 7.60(1H, d, J=2.7Hz), 8.2–10.4(2H, br s), 10.67(1H, br s). $^{13}$C NMR($d_6$-acetone): 97.2, 97.6, 103.2, 107.5, 107.8, 122.9, 126.0, 123.6, 128.2, 136.2, 158.1, 161.2. IR (KBr): 3350, 1626, 1528, 1454, 1361, 1235cm$^{-1}$. HRMS (EI): calcd. for $C_{14}H_8FNO_4$ 273.0437, found 273.0436. |

TABLE 2-continued

| Starting Product | Yield | End Product |
|---|---|---|
| 3-(6-Chloro-1H-indol-3-yl)-2,5-dichloro-[1,4]benzoquinone Blue needles from benzene/hexane. mp 182–183° C.. $^1$H NMR(CDCl$_3$): 7.18(1H, dd, J=1.8, 8.7Hz), 7.23(1H, s), 7.26(1H, s), 7.31(1H, d, J=8.7Hz), 7.44(1H, dd, J=0.6, 1.8Hz), 7.54(1H, d, J=2.7Hz), 8.75(1H, br s). $^{13}$C NMR (d$_6$-acetone): 106.9, 112.0, 117.9, 120.7, 122.8, 124.7, 127.7, 131.3, 133.4, 136.8, 138.6, 143.8, 177.4, 177.8. IR (KBr): 3325, 3122, 3071, 2962, 2926, 1673, 1564, 1517, 1449, 1401, 1020cm$^{-1}$. Anal. Calcd. for C$_{14}$H$_6$Cl$_3$NO$_2$: C, 51.49; H, 1.85; N, 4.29. Found: C, 51.77; H, 1.94; N, 4.21. | 71% | 3-(6-Chloro-1H-indol-3-yl)-2,5-dihydroxy-[1,4]benzoquinone Dark green needles from acetone/hexane. mp 229° C. (dec). $^1$H NMR(d$_6$-acetone): 6.03(1H, s), 7.04(1H, dd, J=1.8, 8.7Hz), 7.50(1H, d, J=1.8Hz), 7.52 1H, d, J=8.7Hz), 7.64(1H, d, J=2.4Hz), 8.4–10.4 (2H, br s), 10.74(1H, br s). $^{13}$C NMR(d$_6$-acetone). 103.2, 105.0, 111.3, 111.4, 119.6, 123.2, 125.6, 127.0, 128.6, 136.8. IR(KBr): 3418, 3305, 2956, 1623, 1534, 1451, 1357, 936cm$^{-1}$. HRMS (EI): calcd. for C$_{14}$H$_8$ClNO$_4$ 289.0142, found 289.0144. |
| 3-(6-Bromo-1H-indol-3-yl)-2,5-dichloro-[1,4]benzoquinone Blue needles from benzene/hexane. mp 180° C.(dec). $^1$H NMR(d$_6$-acetone): 5.15(2H, s), 6.90(1H, dd, J=2.4, 9.0Hz), 7.14(1H, d, J=2.1Hz), 7.26–7.36(3H, m), 7.39(2H, t, J=7.2Hz), 7.50(2H, d, J=7.2Hz), 7.61(1H, d, J=2.4Hz), 10.84(1H, br s). $^{13}$C NMR(d$_6$-acetone): 70.2, 96.6, 106.9, 111.1, 120.4, 122.4, 122.9, 127.6, 127.8, 128.6, 129.6, 129.8, 133.4, 137.2, 138.0, 143.7, 155.8, 177.4, 177.9. IR(KBr): 3396, 3127, 3064, 2946, 2815, 1672, 1651, 1560, 1237, 1011, 819cm$^{-1}$. Anal. Calcd. for C$_{21}$H$_{13}$Cl$_2$NO$_3$: C, 63.34; H, 3.29; N, 3.52. Found: C, 63.07; H, 3.43; N, 3.45. | 83% | 3-(6-Bromo-1H-indol-3-yl)-2,5-dihydroxy-[1,4]benzoquinone Dark green needles from acetone/hexane. mp 205° C. (dec). $^1$H NMR(d$_6$-acetone): 5.14(2H, s), 6.01(1H, s), 6.80(1H, dd, J=2.4, 8.7Hz), 7.07(1H, d, J=2.1Hz), 7.26–7.58(9H, m), 8.4–10.2(2H, br s), 10.44 (1H, br s). $^{13}$C NMR(d$_6$-acetone): 70.2, 96.0, 103.1, 104.7, 110.1, 121.5, 122.7, 126.7, 127.6, 127.7, 128.5, 137.0, 138.2, 155.4. IR(KBr): 3414, 3314, 2925, 1631, 1353, 1299, 1239, 1023, 935cm$^{-1}$. HRMS (EI): calcd. for C$_{21}$H$_{15}$NO$_5$ 361.0950, found 361.0951. |
| 2,5-Dichloro-3-(6-methyl-1H-indol-3-yl)-[1,4]benzoquinone This compound was synthesized according to the general procedure A from 7-methyl-1H-indole(100 mg, 0.762 mmol) and 2,5-dichloro-1,4-benzoquinone(270 mg, 1.52 mmol) and was obtained as a blue solid(188 mg, 81%). mp 169–170° C.. $^1$H NMR(d$_6$-acetone): 2.39(3H, s), 6.92(1H, dd, J=0.8, 4.4Hz), 7.25(1H, d, J=8.4Hz), 7.24–7.26(2H, m), 7.61(1H, d, J=2.8Hz), 10.92(1H, br s). $^{13}$C NMR(d$_6$-acetone): 20.9, 106.6, 112.0, 121.5, 122.1, 123.8, 130.3, 131.9, 133.4, 136.2, 136.9, 139.2, 143.7, 177.7, 178.0. IR (KBr): 3409, 3065, 2918, 1652, 1557, 1256, 1236, 1116, 1015, 878, 805cm$^{-1}$. Anal. Calcd. for C$_{15}$H$_9$Cl$_2$NO$_2$: C, 58.85; H, 2.96. Found: 58.94; H, 3.08. | 82% | 2,5-Dihydroxy-3-(6-methyl-1H-indol-3-yl)-[1,4]benzoquinone Dark green needles from acetone/hexane. mp 190° C. (dec). $^1$H NMR(d$_6$-acetone): 2.37(3H, s), 5.97(1H, s), 6.84(1H, dd, J=1.6, 8.4Hz), 7.20(1H, s), 7.38 (1H, d, J=8.4Hz), 7.48(1H, d, J=2.8Hz), 8.0–10.0 (2H, br s), 10.45(1H, br s). $^{13}$C NMR(d$_6$-acetone): 21.0, 103.2, 104.6, 111.3, 112.3, 121.0, 121.7, 124.8, 127.1, 130.9, 136.8. IR(KBr): 3398, 2919, 2855, 1701, 1617, 1530, 1452, 932cm$^{-1}$. HRMS (EI): calcd. for C$_{15}$H$_{11}$NO$_4$ 269.0688, found 269.0685. |
| 2,5-Dichloro-3-(7-propyl-1H-indol-3-yl)-[1,4]benzoquinone Blue needles from benzene/hexane. mp 187–188° C.. R$_f$=0.31 (3:7, EtOAc/hexane). $^1$H NMR(CDCl$_3$)δ 8.70(bs, NH), 7.55(d, J=3.0Hz, 1H), 7.32(m, 1H), 7.21(s, 1H), 7.11(m, 2H), 2.53(s, 3H). $^1$H NMR(d$_6$-acetone): δ 10.95 (1H, br s), 7.68(1H, m), 7.37(1H, m), 7.25(1H, m), 7.03 (2H, m), 2.55(3H, s). $^{13}$C NMR(d$_6$-acetone): δ 178.0, 177.7, 143.7, 139.3, 136.3, 135.9, 133.4, 130.0, 125.7, 122.9, 121.5, 120.5, 119.4, 107.2, 16.2. IR(KBr): 3403, 3072, 1670, 1563, 1431, 1236, 1037, 750cm$^{-1}$. Anal. Calcd. for C$_{15}$H$_9$Cl$_2$NO$_2$: C, 58.85; H, 2.97; N, 4.58. Found: C, 58.62; H, 2.78; N, 4.53. | 66% | 2,5-Dihydroxy-3-(7-propyl-1H-indol-3-yl)-[1,4]benzoquinone Green crystals from benzene/hexane. mp 218–219° C.. IR(KBr): 3427, 3326, 1618, 1325, 1291, 1185cm$^{-1}$. $^1$H NMR(d$_6$-acetone): δ 10.58(1H, br s), 9.0–10.0 (2H, br), 7.56(1H, d, J=2.7Hz), 7.36(1H, t, J=4.5Hz), 6.95(1H, s), 6.93(1H, s), 6.02(1H, s), 2.52(3H, s). $^{13}$C NMR(d$_6$-acetone): δ 135.8, 127.2, 126.6, 122.1, 120.6, 119.6, 119.5, 112.2, 105.2, 103.2, 16.4. HRMS (FAB) Calcd. For C$_{15}$H$_{11}$NO$_4$ [M$^+$]: 269.0688. Found: 269.0686. |
| 2,5-Dichloro-3-(7-methyl-1H-indol-3-yl)-[1,4]benzoquinone Blue needles from benzene/hexane. mp 140–141° C.. $^1$H NMR(d$_6$-acetone): 1.00(3H, t, J=7.2Hz), 1.77(2H, h, J=7.5Hz), 2.93(2H, dd, J=9.0, 16.5Hz), 7.03(1H, s), 7.06 (1H, t, J=7.2Hz), 7.24(1H, dd, J=1.5, 6.9Hz), 7.34(1H, s), 7.67(1H, dd, J=1.2, 3.0Hz), 11.09(1H, br s). $^{13}$C NMR (d$_6$-acetone): 13.9, 23.6, 33.4, 107.2, 119.5, 120.5, 122.1, 125.9, 126.3, 130.1, 133.4, 135.4, 136.5, 139.2, 143.7, 177.6, 177.9. IR(KBr): 3401, 3062, 2958, 2929, 2871, 2858, 1670, 1572, 1434, 1115, 1023cm$^{-1}$. Anal. Calcd. for C$_{17}$H$_{13}$Cl$_2$NO$_2$: C, 61.10; H, 3.92. Found: C, 60.94; H, 4.13. | 73% | 2,5-Dihydroxy-3-(7-methyl-1H-indol-3-yl)-[1,4]benzoquinone Dark green needles from acetone/hexane. mp 207° C. (dec). $^1$H NMR(d$_6$-acetone): 0.98(3H, t, J=7.6Hz), 1.76(2H, h, J=7.6Hz), 2.89(1H, t, J=7.6Hz), 6.02(1H, s), 6.94–7.00(2H, m), 7.39–7.39(1H, m), 7.54(1H, d, J=2.8Hz), 8.4–10.0(2H, br s), 10.58 1H, br s). $^{13}$C NMR(d$_6$-acetone): 13.7, 23.3, 33.3, 103.2, 105.1, 112.2, 119.4, 119.7, 121.4, 125.4, 126.9, 127.2, 134.3. IR(KBr): 3421, 3330, 2955, 2868, 1615, 1534, 1354, 1297, 1230, 1195cm$^{-1}$. HRMS (EI): calcd. for C$_{17}$H$_{15}$NO$_4$ 297.1001, found 297.1001. |
| 3-(7-tert-butyl-1H-indol-3-yl)-2,5-dichloro-[1,4]benzoquinone Blue needles from benzene/hexane. mp 189–190° C.. $^1$H NMR(d$_6$-acetone): 1.54(9H, s), 7.06(1H, t, J=7.8Hz), 7.15(1H, d, J=6.6Hz), 7.27(1H, d, J=7.8Hz), 7.37(1H, s), 7.64(1H, d, J=3.3Hz), 10.77(1H, br s). $^{13}$C NMR(d$_6$-acetone): 34.5, 106.8, 118.9, 119.3, 120.3, 127.0, 129.5, 133.4, 133.6, 134.4, 137.0, 139.3, 143.7, 177.6, 177.9. IR (KBr): 3438, 3064, 2963, 1659, 1565, 1422, 1269, 1113, 1026, 750cm$^{-1}$. Anal. Calcd. for C$_{18}$H$_{15}$Cl$_2$NO$_2$: C, 62.08; H, 4.34. Found: C, 62.32; H, 4.58. | 83% | 3-(7-tert-butyl-1H-indol-3-yl)-2,5-dihydroxy-[1,4]benzoquinone Dark green needles from acetone/hexane. mp 210–211° C.. $^1$H NMR(d$_6$-acetone): 1.53(9H, s), 6.03 (1H, s), 6.98(1H, t, J=8.0Hz), 7.08(1H, dd, J=1.2, 7.6Hz), 7.36(1H, d, J=8.0Hz), 7.51(1H, d, J=2.8Hz), 9.0–10.0(2H, br s), 10.35(1H, br s). $^{13}$C NMR(d$_6$-acetone): 29.8, 34.2, 103.2, 104.6, 112.0, 118.1, 119.3, 120.1, 126.8, 128.0, 133.5, 133.6. IR (KBr): 3337, 2967, 2866, 1631, 1360, 1299, 1223, 931cm$^{-1}$. HRMS (EI): calcd. for C$_{18}$H$_{17}$NO$_4$ 311.1158, found 311.1158. |

TABLE 2-continued

| Starting Product | Yield | End Product |
|---|---|---|
| 2,5-Dichloro-3-(7-phenyl-1H-indol-3-yl)-[1,4]benzoquinone<br>Blue needles from benzene/hexane. mp 185–186° C.. $^1$H NMR(d$_6$-acetone): 7.21–7.25(2H, m), 7.35(1H, s), 7.38–7.44 (2H, m), 7.47–7.53(2H, m), 7.66(2H, dd, J=1.2, 8.4Hz), 7.70(1H, d, J=2.8Hz), 10.94(1H, br s). $^{13}$C NMR (d$_6$-acetone): 118.0, 119.0, 120.5, 120.9, 121.1, 122.5, 126.7, 127.7, 128.7, 129.2, 130.9, 132.6, 133.5, 133.9, 138.9, 139.1, 143.8, 143.8, 177.6, 178.0. IR(KBr): 3424, 3328, 3137, 3069, 3029, 1675, 1651, 1568, 1426, 755cm$^{-1}$. Anal. Calcd. for C$_{20}$H$_{11}$Cl$_2$NO$_2$: C, 65.24; H, 3.01; N, 3.80. Found: C, 65.44; H, 3.44; N, 3.60. | 76% | 2,5-Dihydroxy-3-(7-phenyl-1H-indol-3-yl)-[1,4]benzoquinone<br>Dark green needles from acetone/hexane. mp 210–211° C.. $^1$H NMR(d$_6$-acetone): 6.04(1H, s), 7.1–7.2 (2H, m), 7.40(1H, t, J=7.4Hz), 7.4–7.7(7H, m), 9.0–10.2(2H, br s), 10.58(1H, br s). $^{13}$C NMR(d$_6$-acetone): 103.3, 105.1, 119.9, 121.3, 121.4, 121.7, 125.9, 127.4, 127.9, 128.1, 128.6, 129.1, 133.8, 139.4. IR(KBr): 3402, 3325, 3029, 2950, 2923, 1633, 1524, 1428, 1343, 760cm$^{-1}$. HRMS (EI): calcd. for C$_{20}$H$_{13}$NO$_4$ 331.0845, found 331.0844. |
| 2,5-Dichloro-3-(7-methoxy-1H-indol-3-yl)-[1,4]benzoquinone<br>Blue needles from benzene/hexane. mp 183–184° C.. $^1$H NMR(CDCl$_3$): 3.94(3H, s), 6.67(1H, d, J=7.6Hz), 6.96 (1H, dd, J=0.8, 8.0Hz), 7.09(1H, t, J=8.0Hz), 7.17(1H, s), 7.50(1H, d, J=3.2Hz), 8.94(1H, br s). $^{13}$C NMR(d$_6$-acetone): 55.1, 102.5, 107.2, 114.4, 120.9, 126.7, 127.4, 129.8, 133.4, 136.7, 139.2, 143.8, 146.9, 177.6, 178.0. IR (KBr): 3391, 3152, 1667, 1626, 1499, 1419, 1114, 1013. Anal. Calcd. for C$_{15}$H$_9$Cl$_2$NO$_3$: C, 55.93; H, 2.82; N, 4.35. Found: C, 56.16; H, 2.94; N, 4.23. | 75% | 2,5-Dihydroxy-3-(7-methoxy-1H-indol-3-yl)-[1,4]benzoquinone<br>Dark green needles from acetone/hexane. mp 202–203° C.. $^1$H NMR(d$_6$-acetone): 3.91(3H, s), 5.98 (1H, s), 6.64(1H, d, J=5.7Hz), 6.91(1H, t, J=6.0Hz), 7.09(1H, d, J=6.0Hz), 7.51(1H, d, J=1.8Hz), 7.8–10.2(2H, br s), 10.63(1H, br s). $^{13}$C NMR (d$_6$-acetone): 55.0, 101.7, 103.2, 105.2, 112.1, 114.8, 119.7, 126.7, 127.1, 128.4, 146.6. IR(KBr): 3390, 3311, 2928, 1634, 1501, 1449, 1354, 1097, 933cm$^{-1}$. HRMS (EI): calcd. for C$_{15}$H$_{11}$NO$_5$ 285.0637, found 285.0636. |
| 3-(7-Benzyloxy-1H-indol-3-yl)-2,5-dichloro-[1,4]benzoquinone<br>Blue needles from benzene/hexane. mp 174–175° C.. $^1$H NMR(d$_6$-acetone): 5.29(2H, s), 6.85(1H, dd, J=1.6, 6.8Hz), 6.99–7.07(2H, m), 7.35(1H, t, J=7.2Hz), 7.36(1H, s), 7.42(2H, dt, J=1.2, 7.2Hz), 7.57(1H, d, J=7.2Hz), 7.66(1H, d, J=2.8Hz), 11.25(1H, br s). $^{13}$C NMR(d$_6$-acetone): 70.0, 103.8, 107.2, 114.6, 120.8, 127.0, 127.6, 127.97, 128.0, 128.6, 129.7, 129.8, 133.4, 137.6, 139.2, 143.8, 146.0, 177.6, 178.0. IR(KBr): 3380, 3066, 2918, 2872, 1674, 1657, 1567, 1428, 1244, 1111cm$^{-1}$. Anal. Calcd. for C$_{21}$H$_{13}$Cl$_2$NO$_3$: C, 63.34; H, 3.29. Found: C, 63.50; H, 3.38. | 84% | 3-(7-Benzyloxy-1H-indol-3-yl)-2,5-dihydroxy-[1,4]benzoquinone<br>Dark green needles from acetone/hexane. mp 202° C. (dec). $^1$H NMR(d$_6$-DMSO): 5.23(2H, s), 5.84(1H, s), 6.38(1H, d, J=7.6Hz), 6.81(1H, d, J=8.0Hz), 6.87(1H, d, J=8.0Hz), 7.26–7.32(2H, m), 7.36 (2H, t, J=7.2Hz), 7.52(2H, d, J=7.6Hz), 9.0–10.0 (2H, br s), 11.42(1H, br s). $^{13}$C NMR(d$_6$-DMSO): 69.8, 103.5, 104.4, 105.5, 112.7, 115.0, 119.6, 126.7, 127.5, 128.2, 128.4, 128.9, 129.1, 138.0, 145.6. IR KBr): 3421, 2960, 2925, 2856, 1631, 1501cm$^{-1}$. HRMS (EI): calcd. for C$_{21}$H$_{15}$NO$_5$ 361.0950, found 361.0950. |
| 3-(7-Fluoro-1H-indol-3-yl)-2,5-dichloro-[1,4]benzoquinone<br>Blue needles from benzene/hexane. mp 177–178° C.. $^1$H NMR(d$_6$-acetone): 6.98(1H, dd, J=8.0, 11.2Hz), 7.09 (1H, dt, J=4.8, 8.0Hz), 7.24(1H, d, J=8.0Hz), 7.40(1H, s), 7.76(1H, d, J=2.8Hz), 11.41(1H, br s). $^{13}$C NMR(d$_6$-acetone): 106.8, 107.0, 117.6, 120.5, 120.6, 130.6, 130.8, 131.1, 132.6, 133.4, 138.8, 143.9, 177.5, 177.9. IR(KBr): 3395, 3096, 1671, 1573, 1503, 1423, 1265, 1236, 1109, 1038cm$^{-1}$. Anal. Calcd. for C$_{14}$H$_6$Cl$_2$FNO$_2$: C, 54.22; H, 1.95. Found: C, 54.36; H, 2.09. | 75% | 3-(7-Fluoro-1H-indol-3-yl)-2,5-dihydroxy-[1,4]benzoquinone<br>Dark blue needles from acetone/hexane. mp 201° C. (dec). IR(KBr): 3420, 3277, 3162, 2923, 2861, 1632, 1357, 1299, 1234cm$^{-1}$. $^1$H NMR(d$_6$-acetone): 6.03 (1H, s), 6.90(1H, dd, J=8.0, 11.6Hz), 6.99(1H, dt, J=4.8, 8.0Hz), 7.34(1H, d, J=8.0Hz), 7.65(1H, J=2.8Hz), 9.0–10.2(2H, br s), 11.00(1H, br s). $^{13}$C NMR(d$_6$-acetone): 103.3, 106.0, 106.2, 111.3, 118.0, 119.3, 119.4, 128.1, 128.3, 130.7. HRMS (EI): calcd. for C$_{14}$H$_8$FNO$_4$ 273.0437, found 273.0440. |
| 3-(7-Chloro-1H-indol-3-yl)-2,5-dichloro-[1,4]benzoquinone<br>Blue needles from benzene/hexane. mp 213–214° C.. $^1$H NMR(d$_6$-acetone): 7.14(1H, t, J=8.0Hz), 7.27(1H, dd, J=0.8, 7.6Hz), 7.40(1H, s), 7.41(1H, dd, J=0.8, 8.0Hz), 7.77(1H, d, J=3.2Hz), 11.23(1H, br s). $^{13}$C NMR(d$_6$-acetone): 108.2, 120.8, 121.4, 122.0, 128.0, 130.9, 131.0, 133.7, 138.9, 144.1, 177.6, 178.1. IR(KBr): 3406, 3071, 2950, 1678, 1649, 1542, 1508, 1434, 1247, 1204cm$^{-1}$. Anal. Calcd. for C$_{14}$H$_6$Cl$_3$NO$_2$: C, 51.49; H, 1.85; N, 4.29. Found: C, 51.59; H, 2.01; N, 4.28. | 70% | 3-(7-Chloro-1H-indol-3-yl)-2,5-dihydroxy-[1,4]benzoquinone Dark blue needles from acetone/hexane. mp 207° C.(dec). $^1$H NMR(d$_6$-acetone): 6.04(1H, s), 7.04(1H, t, J=10.4Hz), 7.20 (1H, d, J=10.0Hz), 7.66(1H, d, J=4.0Hz), 9.0–10.2 (2H, br s), 10.86(1H, br s). $^{13}$C NMR(d$_6$-acetone): 103.4, 106.1, 111.2, 116.4, 120.1, 120.9, 121.0, 128.4, 128.7, 133.3. IR(KBr): 3428, 3310, 3091, 1626, 1354, 1296, 1063, 930cm$^{-1}$. HRMS (EI): calcd. for C$_{14}$H$_8$ClNO$_4$ 289.0142, found 289.0138. |
| 3-(7-Bromo-1H-indol-3-yl)-2,5-dichloro-[1,4]benzoquinone<br>Blue needles from benzene/hexane. mp 191–192° C.. $^1$H NMR(d$_6$-acetone): 7.09(1H, t, J=8.0Hz), 7.41(1H, s), 7.44(2H, dt, J=0.8, 8.0Hz), 7.77(1H, d, J=1.6Hz), 11.14(1H, br s). $^{13}$C NMR(d$_6$-acetone): 104.8, 108.0, 121.0, 121.6, 124.9, 127.5, 130.6, 130.7, 133.4, 138.1, 138.7, 143.9, 177.4, 178.0. IR(KBr): 3368, 3160, 3060, 2972, 2866, 1662, 1561, 1262, 1098, 1012, 882cm$^{-1}$. Anal. Calcd. for C$_{14}$H$_6$BrCl$_2$NO$_2$: C, 45.32; H, 1.63; N, 3.78. Found: C, 45.47; H, 1.75; N, 3.81. | 71% | 3-(7-Bromo-1H-indol-3-yl)-2,5-dihydroxy-[1,4]benzoquinone<br>Dark blue needles from acetone/hexane. mp 225–226° C.. $^1$H NMR(d$_6$-acetone): 6.04(1H, s), 6.99(1H, t, J=7.8Hz), 7.35(1H, dd, J=0.6, 7.8Hz), 7.54(1H, d, J=8.1Hz), 7.66(1H, d, J=2.7Hz), 8.4–10.0(2H, br s), 10.76(1H, br s). $^{13}$C NMR(d$_6$-acetone): 103.4, 104.3, 106.2, 111.3, 120.6, 121.4, 124.1, 128.4, 130.8, 134.7. IR(KBr): 3330, 2959, 2929, 2854, 1617, 1531, 1433, 1354, 1292, 932cm$^{-1}$. HRMS (EI): calcd. for C$_{14}$H$_8$BrNO$_4$ 332.9637, found 332.9637. |

TABLE 2-continued

| Starting Product | Yield | End Product |
|---|---|---|
| 3-(7-Benzyl-1H-indol-3-yl)-2,5-dichloro-[1,4]benzoquinone Blue needles from benzene/hexane. mp 159–160° C.. $^1$H NMR(d$_6$-acetone): 4.30(2H, s), 7.01(1H, d, J=6.6Hz), 7.08(1H, t, J=7.2Hz), 7.14–7.22(1H, m), 7.24–7.33(4H, m), 7.35(1H, s), 7.66(1H, d, J=3.0Hz), 10.95(1H, s). $^{13}$C NMR(d$_6$-acetone): 37.0, 107.3, 117.8, 120.0, 120.6, 122.5, 122.9, 125.0, 126.3, 128.6, 129.0, 130.2, 132.5, 133.4, 135.3, 140.3, 143.7, 177.5, 177.9. IR(KBr): 3414, 3059, 1676, 1656, 1566, 1434, 1266, 1237, 1113, 1033cm$^{-1}$. Anal. Calcd. for C$_{21}$H$_{13}$Cl$_2$NO$_2$: C, 65.99; H, 3.43; N, 3.66. Found: C, 65.74; H, 3.49; N, 3.71. | 85% | 3-(7-Benzyl-1H-indol-3-yl)-2,5-dichloro-[1,4]benzoquinone Dark green needles from acetone/hexane. mp 206–207° C.. $^1$H NMR(d$_6$-acetone): 4.28(2H, s), 6.02 (1H, s), 6.92–7.03(2H, m), 7.14–7.34(5H, m), 7.41 (1H, d, J=7.5Hz), 7.54(1H, d, J=2.7Hz), 8.6–10.3 (2H, br s), 10.49(1H, br s). $^{13}$C NMR(300Hz, d$_6$-acetone): 37.1, 103.2, 105.2, 112.0, 119.6, 120.2, 122.2, 124.1, 126.1, 127.1, 127.4, 128.5, 128.9, 135.2, 140.7. IR(KBr): 3422, 3326, 3084, 3027, 1612, 1532, 1438, 1353cm$^{-1}$. HRMS (EI): calcd. for C$_{21}$H$_{15}$NO$_4$ 345.1001, found 345.1001. |
| 2,5-Dichloro-3-[7-(2-methyl-benzyl)-1H-indol-3-yl]-[1,4]benzoquinone Blue needles from benzene/hexane. mp 101–102° C.. $^1$H NMR(d$_6$-acetone): 2.27(3H, s), 4.28(2H, s), 6.75(1H, d, J=6.9Hz), 7.00–7.23(5, m), 7.30(1H, d, J=8.1Hz), 7.33 (1H, s), 7.68(1H, d, J=3.3Hz), 11.00(1H, br s). $^{13}$C NMR (d$_6$-acetone): 19.1, 34.5, 107.3, 119.9, 120.1, 120.6, 122.0, 122.4, 124.1, 126.0, 126.2, 126.4, 129.4, 130.3, 133.4, 135.5, 136.8, 138.0, 139.2, 143.7, 177.6, 177.9. IR(KBr): 3414, 3060, 2920, 2857, 1656, 1561, 1433, 1237, 1110, 1031cm$^{-1}$. Anal. Calcd. for C$_{22}$H$_{15}$Cl$_2$NO$_{12}$: C, 66.68; H, 3.82; N, 3.53. Found: C, 65.88; H, 3.85; N, 3.79. | 96% | 2,5-Dihydroxy-3-[7-(2-methyl-benzyl)-1H-indol-3-yl]-[1,4]benzoquinone Dark green needles from acetone/hexane. mp 220° C. (dec). $^1$H NMR(d$_6$-acetone): 2.27(3H, s), 4.25(2H, s), 6.02(1H, s), 6.70(1H, d, J=7.2Hz), 6.92–7.04 (2H, m), 7.05–7.15(2H, m), 7.18(1H, t, J=7.2Hz), 7.56(1H, d, J=2.4Hz), 8.8–10.2(2H, br s), 10.56 (1H, br s). $^{13}$C NMR(d$_6$-acetone): 19.1, 34.6, 103.2, 105.2, 112.1, 119.5, 120.2, 121.6, 123.2, 126.1, 126.5, 126.9, 127.4, 129.4, 130.2, 135.4, 136.8, 138.3. IR(KBr): 3304, 2966, 1699, 1624, 1434, 1350, 1218cm$^{-1}$. HRMS (EI): calcd. for C$_{22}$H$_{17}$NO$_4$ 359.1158, found 359.1157. |
| 3-(1H-Benzo[g]indol-3-yl)-2,5-dichloro-[1,4]benzoquinone Blue needles from benzene/hexane. mp 210–211° C.. $^1$H NMR(d$_6$-acetone): 7.18–7.25(1H, m), 7.38–7.62(6H, m), 7.72–7.75(1H, m), 7.97(1H, d, J=8.1Hz), 8.49(1H, d, J=8.1Hz), 11.85(1H, br s). $^{13}$C NMR(d$_6$-acetone): 111.0, 118.0, 119.8, 120.4, 120.9, 121.3, 124.0, 124.4, 125.9, 127.8, 128.7, 133.4. IR(KBr): 3340, 3063, 2922, 1675, 1651, 1558, 1272, 1224, 1021, 871cm$^{-1}$. HRMS (FAB) : calculated for C$_{18}$H$_9$Cl$_2$NO$_2$ 341.0010. Found 341.0013. | 70% | 3-(1H-Benzo[g]indol-3-yl)-2,5-dihydroxy-[1,4]benzoquinone Dark green needles from acetone/hexane. mp 210° C. (dec). $^1$H NMR(d$_6$-acetone): 6.05(1H, s), 7.42(1H, dt, J=1.5, 6.9Hz), 7.45–7.56(2H, m), 7.60–7.68 (2H, m), 7.93(1H, d, J=8.1Hz), 8.36(1H, d, J=8.1Hz), 8.8–10.5(2H, br s), 11.51(1H, br s). $^{13}$C NMR(d$_6$-acetone): 103.2, 106.4, 111.9, 119.8, 120.3, 122.1, 122.4, 123.9, 125.4, 128.6, 130.5, 130.8. IR (KBr): 3318, 3158, 3060, 2923, 2855, 1612, 1353, 1291, 929, 814cm$^{-1}$. HRMS (FAB) : calcd. for C$_{18}$H$_{11}$NO$_4$ 305.0688, found 305.0686. |
| 3-(2,6-Dimethyl-1H-indol-3-yl)-2,5-dichloro-[1,4]benzoquinone Blue needles from benzene/hexane. mp 114–115° C.. $^1$H NMR(d$_6$-acetone): 2.34(3H, s), 2.39(3H, s), 6.86(1H, d, J=8.7Hz), 7.12(1H, d, J=8.1Hz), 7.17(1H, s), 7.37(1H, s), 10.46(1H, br s). $^{13}$C NMR(d$_6$-acetone): 13.0, 21.1, 102.6, 111.0, 119.6, 121.5, 125.4, 130.9, 133.4, 136.4, 136.8, 140.1, 144.0, 176.9, 178.1. IR(KBr): 3266, 3064, 2958, 2921, 1677, 1654, 1568, 1466, 1258, 1033cm$^{-1}$. Anal. Calcd. for C$_{16}$H$_{11}$Cl$_2$NO$_2$: C, 60.02; H, 3.46; N, 4.37. Found: C, 59.76; H, 3.54; N, 4.32. | 73% | 3-(2,6-Dimethyl-1H-indol-3-yl)-2,5-dihydroxy-[1,4]benzoquinone Dark green needles from acetone/hexane. mp 210° C. (dec). $^1$H NMR(d$_6$-acetone): 2.28(3H, s), 2.37(3H, s), 6.03(1H, s), 6.78(1H, d, J=8.7Hz), 7.07–7.14 (2H, m), 8.4–9.9(2H, br s), 10.09(1H, br s). $^{13}$C NMR(d$_6$-acetone): 12.8, 21.2, 103.4, 110.5, 119.6, 120.7, 126.5, 129.9, 134.8, 136.4. IR(KBr): 3384, 3324, 2975, 2912, 2857, 1637, 1352, 1295, 1228, 1184cm$^{-1}$. HRMS (EI): calcd. for C$_{16}$H$_{13}$NO$_4$ 283.0845, found 283.0849. |
| 3-(2,7-Dimethyl-1H-indol-3-yl)-2,5-dichloro-[1,4]benzoquinone Blue needles from benzene/hexane. mp 95–96° C.. $^1$H NMR (d$_6$-acetone): 2.35(3H, s), 2.49(3H, s), 6.86–6.96(2H, m), 7.07(1H, d, J=6.9Hz), 7.36(1H, s), 10.51(1H, br s). $^{13}$C NMR(d$_6$-acetone): 13.1, 16.4, 105.4, 117.6, 120.1, 120.4, 122.2, 127.2, 133.4, 135.4, 137.2, 139.8, 140.1, 144.0, 176.9, 178.1. IR(KBr): 3362, 3064, 2919, 2860, 1675, 1620, 1453, 1269, 1243, 884cm$^{-1}$. Anal. Calcd. for C$_{16}$H$_{11}$Cl$_2$NO$_2$: C, 60.02; H, 3.46; N, 4.37. Found: C, 60.19; H, 3.59; N, 4.31. | 84% | 3-(2,7-Dimethyl-1H-indol-3-yl)-2,5-dihydroxy-[1,4]benzoquinone Dark green needles from acetone/hexane. mp 206° C. (dec). $^1$H NMR(d$_6$-acetone): 2.32(3H, s), 2.47(3H, s), 6.05(1H, s), 6.85(1H, s), 6.88(1H, d, J=7.2Hz), 7.07(1H, dd, J=2.1, 7.2Hz), 8.5–10.0(2H, br s), 10.16(1H, br s). $^{13}$C NMR(d$_6$-acetone): 12.8, 16.4, 102.6, 103.4, 112.0, 117.6, 119.2, 119.7, 121.3, 128.2, 135.2, 135.4. IR(KBr): 3331, 2945, 2856, 1629, 1559, 1454, 1185, 932cm$^{-1}$. HRMS (EI): calcd. for C$_{16}$H$_{13}$NO$_4$ 283.0845, found 283.0846. |
| 3-(6,7-Dimethyl-1H-indol-3-yl)-2,5-dichloro-[1,4]benzoquinone Blue needles from benzene/hexane. mp 184–185° C.. IR (KBr): 3387, 3071, 2920, 2860, 1675, 1551, 1506, 1433, 1263cm$^{-1}$. $^1$H NMR(d$_6$-acetone)2.36(3H, s), 2.46(3H, s), 6.95(1H, d, J=8.4Hz), 7.12(1H, d, J=8.0Hz), 7.33(1H, s), 7.61(1H, d, J=2.8Hz), 10.84(1H, s). $^{13}$C NMR(d$_6$-acetone): 12.6, 18.6, 107.2, 118.9, 119.2, 123.1, 124.0, 129.6, 130.0, 133.4, 136.6, 139.1, 143.6, 177.7, 178.0. Anal. Calcd. for C$_{16}$H$_{11}$Cl$_2$NO$_2$: C, 60.02; H, 3.46; N, 4.37. Found: C, 59.98; H, 3.59; N, 4.23 | 75% | 3-(6,7-Dimethyl-1H-indol-3-yl)-2,5-dihydroxy-[1,4]benzoquinone Dark green needles from acetone/hexane. mp 220° C. (dec). $^1$H NMR(d$_6$-acetone): 2.35(3H, s), 2.43(3H, s), 6.01(1H, s), 6.86(1H, d, J=8.1Hz), 7.25(1H, d, J=7.8Hz), 7.50(1H, d, J=2.7Hz), 8.8–10.2(2H, br s), 10.38(1H, br s). $^{13}$C NMR(d$_6$-acetone): 12.7, 18.8, 103.1, 118.2, 112.5, 119.1, 122.2, 123.1, 125.0, 126.9, 128.6, 129.9. IR(KBr): 3340, 3150, 2921, 2869, 1615, 1533, 1351cm$^{-1}$. HRMS (EI): calcd. for C$_{16}$H$_{13}$NO$_4$ 283.0845, found 283.0850. |

TABLE 2-continued

| Starting Product | Yield | End Product |
|---|---|---|
| 3-(5,6-Methylenedioxy-1H-indol-3-yl)-2,5-dichloro-[1,4]benzoquinone<br>Blue needles from benzene/hexane. mp 170° C.(dec). $^1$H NMR(d$_6$-acetone): 5.95(2H, s), 6.82(1H, s), 6.99(1H, s), 7.34(1H, s), 7.54(1H, d, J=3.0Hz), 10.82(1H, br s). $^{13}$C NMR(d$_6$-acetone): 92.6, 100.3, 101.0, 107.1, 120.2, 128.9, 131.3, 133.3, 136.4, 139.2, 143.6, 143.7, 145.3, 177.6, 178.0. IR(KBr): 3337, 3066, 2971, 2874, 1668, 1566, 1426, 1042, 942cm$^{-1}$. Anal. Calcd. for C$_{15}$H$_7$Cl$_2$NO$_4$: C, 53.60; H, 2.10. Found: C, 53.61; H, 2.23. | 57% | 3-(5,6-Methylenedioxy-1H-indol-3-yl)-2,5-dihydroxy-[1,4]benzoquinone<br>Dark green needles from acetone/hexane. mp 335° C. (dec). $^1$H NMR(d$_6$-acetone): 5.91(2H, s), 6.00(1H, s), 6.92(1H, d, J=0.8Hz), 6.94(1H, d, J=0.4Hz), 7.44(1H, d, J=2.8Hz), 8.8–10.2(2H, br s), 10.42 (1H, br s). $^{13}$C NMR(d$_6$-acetone): 92.4, 100.6, 100.64, 100.8, 103.0, 109.8, 126.2, 126.3, 131.2, 142.8, 144.7. IR(KBr): 3420, 3077, 2937, 2844, 1624, 1470, 1330cm$^{-1}$. HRMS (EI): calcd. for C$_{15}$H$_9$NO$_6$ 299.0430, found 299.0428. |
| 3-(5,6-Dimethoxy-1H-indol-3-yl)-2,5-dichloro-[1,4]benzoquinone<br>Blue needles from benzene/hexane mp 186–187° C.. IR (KBr): 3300, 3040, 2952, 2957, 2829, 1634, 1546, 1484, 1228, 1087cm$^{-1}$. $^1$H NMR(d$_6$-acetone): 3.78(3H, s), 3.84 (3H, s), 6.93(1H, s), 7.10(1H, s), 7.36(1H, s), 7.56(1H, d, J=2.7Hz), 10.82(1H, br s). $^{13}$C NMR(d$_6$-acetone): 55.7, 56.0, 95.8, 104.7, 106.8, 117.6, 119.0, 120.6, 129.1, 130.8, 133.4, 143.6, 145.9, 147.9, 177.7, 177.9. Anal. Calcd. for C$_{16}$H$_{11}$Cl$_2$NO$_4$: C, 54.57; H, 3.15. Found: C, 51.03; H, 3.32. | 65% | 3-(5,6-Dimethoxy-1H-indol-3-yl)-2,5-dihydroxy-[1,4]benzoquinone<br>Dark green needles from acetone/hexane. mp 335° C. (dec). $^1$H NMR(d$_6$-acetone): 5.91(2H, s), 6.00(1H, s), 6.92(1H, d, J=0.8Hz), 6.94(1H, d, J=0.4Hz), 7.44(1H, d, J=2.8Hz), 8.8–10.2(2H, br s), 10.42 (1H, br s). $^{13}$C NMR(d$_6$-acetone): 92.4, 100.6, 100.64, 100.8, 103.0, 109.8, 126.2, 126.3, 131.2, 142.8, 144.7. IR(KBr): 3420, 3077, 2937, 2844, 1624, 1470, 1330cm$^{-1}$. HRMS (EI): calcd. for C$_{15}$H$_9$NO$_6$ 299.0430, found 299.0428. |

EXAMPLE 7

Inhibition of Phosphatase Cdc25B

Using procedures known to those skilled in the art, the compounds listed in Table 3 were screened against Cdc25A, Cdc25B, and Cdc25C at 50 μM. Similar amounts of inhibition were seen for all three isoforms of Cdc25. To analyze these effects further, the compounds were then screened against Cdc25B in a 3 pt. IC-50, using 1, 7 and 50 μM. Several of the compounds were also screened with an 8 pt. IC-50 process, using 0.1–10 μM, allowing determination of Hill slopes. Further data (not shown) demonstrates that these compounds are competitive vs. substrate, indicating that they bind at the active site of Cdc25. Overall, these results show that these are preferred compound for treating a Cdc25-related cell proliferative disorder.

TABLE 3

| CHEMISTRY | plate No. | Ser. No. | IC50 (3 pt) | IC50 (8 pt) | Percent Inhibition at 50 uM compound | | |
|---|---|---|---|---|---|---|---|
| | | | | | Cdc25 A | Cdc25 B | Cdc25 C |
| 2,5-dihydroxy-3(1H-indol-3-yl)-[1,4]-benzoquinone | 2A | ZL-I-197 | 14.2 | 16.5 | 55 | 75 | 69 |
| 2,5-dihydroxy-3-(1-methyl-1H-indol-3-yl)-[1,4]-benzoquinone | 2B | ZL-I-194 | 184.5 | | 63 | 42 | 19 |
| 2,5-dihydroxy-3-(2-methyl-1H-indol-3-yl)-[1,4]-benzoquinone | 2C | ZL-I-186 | 138.3 | | 35 | 9 | 5 |
| 2,5-dihydroxy-3-(2-ethyl-1H-indol-3-yl)-[1,4]-benzoquinone | 2D | ZL-I-174 | 33.4 | | 51 | 36 | 14 |
| 2,5-dihydroxy-3-(2-cyclopropyl-1H-indol-3-yl)-[1,4]-benzoquinone | 2E | ZL-I-184 | 2.3 | 24.4 | 79 | 32 | 0 |
| 2,5-dihydroxy-3-(2-isopropyl-1H-indol-3-yl)-[1,4]-benzoquinone | 2F | ZL-I-185 | 8.3 | | 58 | 13 | 0 |
| 2,5-dihydroxy-3-[2-(1-methylcycloproyl)-1H-indol-3-yl]-[1,4]-benzoquinone | 2G | LD-I-205 | 3.6 | | 49 | 17 | 0 |
| 2,5-dihydroxy-3-(2-tert-butyl-1H-indol-3-yl)-[1,4]-benzoquinone | 2H | ZL-I-187 | 13.9 | | 31 | 11 | 0 |
| 2,5-dihydroxy-3-[2-(1-methylcyclohexyl)-1H-indol-3-yl]-[1,4]-benzoquinone | 3A | LD24B | 82.9 | | 69 | 11 | 22 |
| 2,5-dihydroxy-3-(2-phenyl-1H-indol-3-yl)-[1,4]-benzoquinone | 3B | ZL-I-207 | 22.2 | | 93 | 38 | 18 |
| 2,5-dihydroxy-3-[2-(1,1-dimethyl-allyl)-1H-indol-3-yl]-[1,4]-benzoquinone | 3C | ZL-I-202 | 40.3 | | 40 | 0 | 21 |
| 2,5-dihydroxy-3-(4-fluoro-1H-indol-3-yl)-[1,4]-benzoquinone | 3D | LD-I-217 | 1.2 | 15.9 | 59 | 5 | 0 |
| 2,5-dihydroxy-3-(4-chloro-1H-indol-3-yl)-[1,4]-benzoquinone | 3E | LD9B | 3.0 | 8.4 | 67 | 21 | 0 |
| 2,5-dihydroxy-3-(4-bromo-1H-indol-3-yl)-[1,4]-benzoquinone | 3F | LD11B | 3.1 | >2 | 0 | 6 | 54 |
| 2,5-dihydroxy-3-(4-methoxy-1H-indol-3-yl)-[1,4]-benzoquinone | 3G | LD19B | 7.2 | | 77 | 21 | 19 |

TABLE 3-continued

| CHEMISTRY | plate No. | Ser. No. | IC50 (3 pt) | IC50 (8 pt) | Percent Inhibition at 50 uM compound | | |
|---|---|---|---|---|---|---|---|
| | | | | | Cdc25 A | Cdc25 B | Cdc25 C |
| 2,5-dihydroxy-3-(4-benzyloxy-1H-indol-3-yl)-[1,4]-benzoquinone | 3H | LD-I-90 | 4.6 | | 87 | 0 | 2 |
| 2,5-dihydroxy-3-(4-methyl-1H-indol-3-yl)-[1,4]-benzoquinone | 4A | LD13B | 6.0 | | 51 | 9 | 28 |
| 2,5-dihydroxy-3-(5-fluoro-1H-indol-3-yl)-[1,4]-benzoquinone | 4B | LD-I-204 | 11.7 | | 64 | 32 | 23 |
| 2,5-dihydroxy-3-(5-chloro-1H-indol-3-yl)-[1,4]-benzoquinone | 4C | LD3B | 2.3 | | 95 | 32 | 45 |
| 2,5-dihydroxy-3-(5-bromo-1H-indol-3-yl)-[1,4]-benzoquinone | 4D | LD6B | 2.4 | | 96 | 55 | 26 |
| 2,5-dihydoxy-3-(7-methyl-1H-indol-3-yl)-[1,4]naphthoquinone | 4E | ZL-III-198 | 69.3 | | 10 | 0 | 0 |
| 2,5-dihydroxy-3-(5-methoxy-1H-indol-3-yl)-[1,4]-benzoquinone | 4F | LD2B | 6.0 | | 15 | 0 | 0 |
| 2,5-dihydroxy-3-(5-benzyloxy-1H-indol-3-yl)-[1,4]-benzoquinone | 4G | LD4B | 1.8 | | 96 | 50 | 26 |
| 2,5-dihydroxy-3-(5-methyl-1H-indol-3-yl)-[1,4]-benzoquinone | 4H | LD20B | 2.5 | | 94 | 61 | 55 |
| 2,5-dihydroxy-3-(6-fluoro-1H-indol-3-yl)-[1,4]-benzoquinone | 5A | LD-I-210 | 2.0 | 6.8 | 91 | 48 | 90 |
| 2,5-dihydroxy-3-(6-chloro-1H-indol-3-yl)-[1,4]-benzoquinone | 5B | LD1B | 2.4 | | 99 | 92 | 81 |
| 2,5-dihydroxy-3-(6-benzyloxy-1H-indol-3-yl)-[1,4]-benzoquinone | 5C | LD-I-214 | 1.7 | | 89 | 97 | 92 |
| 2,5-dihydroxy-3-(6-methyl-1H-indol-3-yl)-[1,4]-benzoquinone | 5D | LD10B | 32.3 | | 80 | 16 | 28 |
| 2,5-dimethoxy-3-(7-fluoro-1H-indol-3-yl)-[1,4]-benzoquinone | 5E | LD-I-206 | 125.1 | | 29 | 67 | 68 |
| 2,5-dihydroxy-3-(7-chloro-1H-indol-3-yl)-[1,4]-benzoquinone | 5F | LD-I-207 | 38.0 | | 92 | 23 | 54 |
| 2,5-dihydroxy-3-(7-bromo-1H-indol-3-yl)-[1,4]-benzoquinone | 5G | LD-I-216 | 2.1 | | 93 | 45 | 88 |
| 2,5-dihydroxy-3-(7-methyl-1H-indol-3-yl)-[1,4]-benzoquinone | 5H | ZL-I-175 | 4.2 | | 60 | 0 | 1 |
| 2,5-dihydroxy-3-(7-propyl-1H-indol-3-yl)-[1,4]-benzoquinone | 6A | LD-I-215 | 14.1 | | 93 | 23 | 79 |
| 2,5-dihydroxy-3-(7-prenyl-1H-indol-3-yl)-[1,4]-benzoquinone | 6B | ZL-I-196 | 2.1 | | 100 | 99 | 84 |
| 2,5-dihydroxy-3-(7-geranyl-1H-indol-3-yl)-[1,4]-benzoquinone | 6C | LD25B | 0.1 | 0.5 | 99 | 95 | 96 |
| 2,5-dihydroxy-3-(7-farnecyl-1H-indol-3-yl)-[1,4]-benzoquinone | 6D | LD26B | 0.1 | 0.5 | 86 | 89 | 85 |
| 2,5-dihydroxy-3-(7-benzyl-1H-indol-3-yl)-[1,4]-benzoquinone | 6E | LD-I-219 | 1.7 | | 98 | 97 | 98 |
| 2,5-dihydroxy-3-[7-(2-methyl-benzyl)-1H-indol-3-yl]-[1,4]-benzoquinone | 6F | LD-I-218 | 0.6 | 1.1 | 90 | 97 | 94 |
| 2,5-dihydroxy-3-(7-tert-butyl-1H-indol-3-yl)-[1,4]-benzoquinone | 6G | LD22B | 2.1 | | 96 | 33 | 37 |
| 2,5-dihydroxy-3-(7-phenyl-1H-indol-3-yl)-[1,4]-benzoquinone | 6H | LD-I-143 | 1.4 | | 98 | 92 | 91 |
| 2,5-dihydroxy-3-(7-methoxy-1H-indol-3-yl)-[1,4]-benzoquinone | 7A | LD8B | 79.5 | | 36 | 15 | 13 |
| 2,5-dihydroxy-3-(7-benzyloxy-1H-indol-3-yl)-[1,4]-benzoquinone | 7B | LD17B | 1.6 | | 98 | 97 | 85 |
| 2,5-dihydroxy-3-(2,5-dimethyl-1H-indol-3-yl)-[1,4]-benzoquinone | 7C | ZL-I-199 | 16.5 | | 61 | 20 | 25 |
| 2,5-dihydroxy-3-(2-methyl-5-methoxy-1H-indol-3-yl)-[1,4]-benzoquinone | 7D | ZL-I-192 | 125.9 | | 0 | 0 | 31 |
| 2,5-dihydroxy-3-(2-methyl-5-chloro-1H-indol-3-yl)-[1,4]-benzoquinone | 7E | ZL-I-193 | 52.2 | | 91 | 60 | 81 |
| 2,5-dihydroxy-3-(2,6-dimethyl-1H-indol-3-yl)-[1,4]-benzoquinone | 7F | LD-I-209 | 206.7 | | 46 | 16 | 0 |
| 2,5-dihydroxy-3-(2,7-dimethyl-1H-indol-3-yl)-[1,4]-benzoquinone | 7G | LD15B | 38.5 | | 20 | 0 | 0 |
| 2,5-dihydroxy-3-(5,6-methylenedioxy-1H-indol-3-yl)-[1,4]-benzoquinone | 7H | LD-I-125 | 3.7 | | 96 | 88 | 63 |
| 2,5-dihydroxy-3-(5,6-dimethoxy-1H-indol-3-yl)-[1,4]-benzoquinone | 8A | LD16B | 116.9 | | 39 | 19 | 20 |
| 2,5-dihydroxy-3-(6,7-dimethyl-1H-indol-3-yl)-[1,4]-benzoquinone | 8B | LD-I-208 | 12.8 | | 90 | 32 | 20 |

TABLE 3-continued

| CHEMISTRY | plate No. | Ser. No. | IC50 (3 pt) | IC50 (8 pt) | Percent Inhibition at 50 uM compound | | |
|---|---|---|---|---|---|---|---|
| | | | | | Cdc25 A | Cdc25 B | Cdc25 C |
| 2,5-dihydroxy-3-(1H-benzo[g]indol-3-yl)-[1,4]-benzoquinone | 8C | LD-I-213 | 2.8 | | 98 | 79 | 75 |
| 2-(2-tert-butyl-1H-indol-3-yl)-5-(7-tert-butyl-1H-indol-3-yl)-3-chloro-6-hydroxy-[1,4]-benzoquinone | 8D | ZL-III-273-I | 5.8 | | | | |
| DAQ-B1 | 8E | ZL-II-241 | 0.9 | | | | |
| 2-(2-tert-butyl-1H-indol-3-yl)-3,6-dihydroxy-5-(1H-indol-3-yl)-[1,4]-benzoquinone | 8F | ZL-III-268 | 11.2 | | | | |
| 2-(2-tert-butyl-1H-indol-3-yl)-3,6-dihydroxy-5-(1-methyl-1H-indol-3-yl)-[1,4]-benzoquinone | 8G | ZL-III-269 | 12.0 | | | | |
| 2-(2-tert-butyl-1H-indol-3-yl)-3,6-dihydroxy-5-(2-methyl-1H-indol-3-yl)-[1,4]-benzoquinone | 8H | ZL-II-193 | 5.8 | | | | |
| 2-(2-tert-butyl-1H-indol-3-yl)-3,6-dihydroxy-5-(2-cyclopropyl-1H-indol-3-yl)-[1,4]-benzoquinone | 9A | ZL-III-262 | 5.6 | | | | |
| 2-(2-tert-butyl-1H-indol-3-yl)-3,6-dihydroxy-5-(2-isopropyl-1H-indol-3-yl)-[1,4]-benzoquinone | 9B | ZL-III-261 | 5.0 | | | | |
| 2-(2-tert-butyl-1H-indol-3-yl)-3,6-dihydroxy-5-(2-tert-butyl-1H-indol-3-yl)-[1,4]-benzoquinone | 9C | ZL-III-263 | 5.1 | | | | |
| 2-(2-tert-butyl-1H-indol-3-yl)-3,6-dihydroxy-5-(2-phenyl-1H-indol-3-yl)-[1,4]-benzoquinone | 9D | ZL-III-260 | 6.1 | | | | |
| 2-(2-tert-butyl-1H-indol-3-yl)-3,6-dihydroxy-5-(4-methoxy-1H-indol-3-yl)-[1,4]-benzoquinone | 9E | ZL-III-278 | 13.7 | | | | |
| 2-(2-tert-butyl-1H-indol-3-yl)-3,6-dihydroxy-5-(4-benzyloxy-1H-indol-3-yl)-[1,4]-benzoquinone | 9F | ZL-III-277 | 2.3 | | | | |
| 2-(2-tert-butyl-1H-indol-3-yl)-3,6-dihydroxy-5-(5-fluoro-1H-indol-3-yl)-[1,4]-benzoquinone | 9G | ZL-III-275 | 8.7 | | | | |
| 2-(2-tert-butyl-1H-indol-3-yl)-3,6-dihydroxy-5-(5-methoxyl-1H-indol-3-yl)-[1,4]-benzoquinone | 9H | ZL-III-270 | 80.3 | | | | |
| 2-(2-tert-butyl-1H-indol-3-yl)-3,6-dihydroxy-5-(5-benzyloxy-1H-indol-3-yl)-[1,4]-benzoquinone | 10A | ZL-III-271 | 0.6 | | | | |
| 2-(2-tert-butyl-1H-indol-3-yl)-3,6-dihydroxy-5-(5-methyl-1H-indol-3-yl)-[1,4]-benzoquinone | 10B | ZL-III-272 | 7.2 | | | | |
| 2-(2-tert-butyl-1H-indol-3-yl)-3,6-dihydroxy-5-(6-fluoro-1H-indol-3-yl)-[1,4]-benzoquinone | 10C | ZL-III-276 | 5.3 | | | | |
| 2-(2-tert-butyl-1H-indol-3-yl)-3,6-dihydroxy-5-(6-methyl-1H-indol-3-yl)-[1,4]-benzoquinone | 10D | ZL-III-279 | 5.3 | | | | |
| 2-(2-tert-butyl-1H-indol-3-yl)-3,6-dihydroxy-5-(7-methyl-1H-indol-3-yl)-[1,4]-benzoquinone | 10E | ZL-III-267 | 4.8 | | | | |
| 2-(2-tert-butyl-1H-indol-3-yl)-3,6-dihydroxy-5-(7-tert-butyl-1H-indol-3-yl)-[1,4]-benzoquinone | 10F | ZL-III-273 | 0.9 | | | | |
| 2-(2-tert-butyl-1H-indol-3-yl)-3,6-dihydroxy-5-(2,5-dimethyl-1H-indol-3-yl)-[1,4]-benzoquinone | 10G | ZL-III-264 | 14.6 | | | | |
| 2-(2-tert-butyl-1H-indol-3-yl)-3,6-dihydroxy-5-(2-methyl-5-methoxy-1H-indol-3-yl)-[1,4]-benzoquinone | 10H | ZL-III-266 | 11.5 | | | | |
| 2-(2-tert-butyl-1H-indol-3-yl)-3,6-dihydroxy-5-(2-methyl-5-chloro-1H-indol-3-yl)-[1,4]-benzoquinone | 11A | ZL-III-265 | 8.4 | | | | |
| 2,5-dihydroxy-3-(1-methyl-1H-indol-3-yl)-6-phenyl-[1,4]-benzoquinone | 11B | ZL-III-185 | 7.9 | | | | |
| 2,5-dihydroxy-3,6-bis(2-methyl-1H-indol-3-yl)-[1,4]-benzoquinone | 11C | ZL-III-274 | 15.7 | | | | |
| 2,5-dihydoxy-3-(2-methyl-1H-indol-3-yl)-[1,4]naphthoquinone | 11D | ZL-III-168-II | 18.0 | | | | |
| 2,5-bis(2-tert-butyl-1H-indol-3-yl)-3-chloro-6-hydroxy-[1,4]-benzoquinone | 11E | ZL-III-263-I | 22.9 | | | | |
| 2-(2-tert-butyl-1H-indol-3-yl)-5-(1H-indol-3-yl)-3-chloro-6-hydroxy-[1,4]-benzoquinone | 11F | ZL-III-268-I | 49.9 | | | | |
| 2-(2-tert-butyl-1H-indol-3-yl)-5-(7-methyl-1H-indol-3-yl)-3-chloro-6-hydroxy-[1,4]-benzoquinone | 11G | ZL-III-267-I | 33.8 | | | | |
| 2-(2-tert-butyl-1H-indol-3-yl)-5-(2-phenyl-1H-indol-3-yl)-3-chloro-6-hydroxy-[1,4]-benzoquinone | 11H | ZL-III-260-I | 6.7 | | | | |

EXAMPLE 8

Inhibition of Phosphatase H1

Using procedures known to those skilled in the art, the compounds listed in Table 3 were screened against recombinant vaccinia H1 phosphatase using FMOP as a fluorogenic substrate. Compounds were initially screened at 1 micromolar concentration. Several compounds in this series completely abolish enzymatic activity at this concentration, while the majority of compounds have low enzyme inhibition activity.

The foregoing is illustrative of the present invention, and is not to be construed as limiting thereof. The invention is defined by the following claims, with equivalents of the claims to be included therein.

What is claimed is:

1. An acid-catalyzed method of producing a compound of formula I:

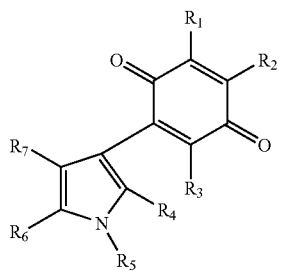

wherein:
- $R_1$ and $R_3$ are each chlorine;
- $R_2$ is hydrogen, aryl, alkyl, alkoxy, phenoxy, anilino, amino, halo, acyloxy, or (acyloxy)alkyl;
- $R_5$ is hydrogen, $C_1$–$C_7$ alkyl, $C_2$–$C_7$ alkenyl, $C_2$–$C_7$ alkynyl, arylalkyl, or aryl;
- $R_4$ is, alkylcarboxy, $C_2$–$C_m$ alkenyl, alkynyl, alkenylcarboxy, hydroxy, hydroxyalkyl, $C_1$–$C_n$ alkoxy, nitro, halo, trihalomethyl, amido, carboxamido, carboxy, sulfonyl, sulfonamido, amino, mercapto, or 2-methylbut-2-en-4-yl, wherein n is an integer from 2–12, and m is an integer from 3–12; and
- $R_6$ and $R_7$ form part of an aromatic ring wherein said aromatic ring may be substituted;

which method comprises:
reacting a substituted or unsubstituted 2,5-dichloro-1,4-benzoquinone compound of formula II:

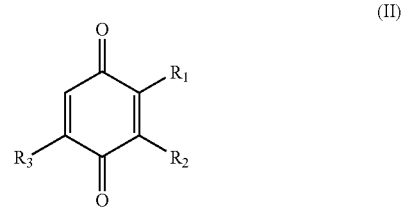

wherein $R_1$, $R_2$ and $R_3$ are as defined above;
with at least one pyrrole of the formula III:

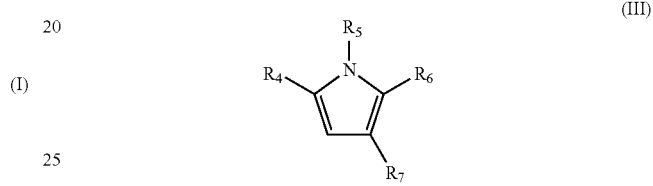

wherein $R_4$–$R_7$ are as defined above;
in a polar organic solvent and in the presence of an acid to produce a first intermediate; and then
reacting the first intermediate with an oxidization agent to produce said compound of formula I.

2. The method of claim 1, wherein n is 2–7 and m is 3–7.

3. The method of claim 1, wherein the organic solvent is an aprotic solvent selected from the group consisting of tetrahydrofuran (THF), acetonitrile, and mixtures thereof.

4. The method of claim 1, wherein the acid is HCl.

5. The method of claim 1, wherein the acid is $H_2SO_4$.

6. The method of claim 1, wherein the acid is AcOH.

7. The method of claim 1, wherein the oxidization agent is dichlorodicyanobenzoquinone.

8. The method of claim 1, wherein the oxidization agent is $Ag_2CO_3$.

9. The method of claim 1, wherein the reaction is conducted at a temperature from about −10° C. to about 100° C.

* * * * *